(12) United States Patent
Horvath et al.

(10) Patent No.: US 12,331,544 B2
(45) Date of Patent: *Jun. 17, 2025

(54) DEVICE FOR AUTOMATICALLY CLEANING A HANDLE

(71) Applicant: CleanMotion Sàrl, Lausanne (CH)

(72) Inventors: Alex Horvath, Lausanne (CH); Valentin Van Sprolant, Bonne (FR); Giovanni Barilla, Geneva (CH)

(73) Assignee: CleanMotion Sàrl, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/624,803

(22) Filed: Apr. 2, 2024

(65) Prior Publication Data
US 2024/0328194 A1 Oct. 3, 2024

Related U.S. Application Data

(62) Division of application No. 17/425,265, filed as application No. PCT/EP2020/051690 on Jan. 23, 2020, now Pat. No. 11,982,101.

(30) Foreign Application Priority Data

Jan. 24, 2019 (EP) .................................... 19153558

(51) Int. Cl.
*E05B 1/00* (2006.01)
*A61L 2/18* (2006.01)
(Continued)

(52) U.S. Cl.
CPC .............. *E05B 1/0069* (2013.01); *A61L 2/18* (2013.01); *A61L 2/235* (2013.01); *A61L 2/24* (2013.01);
(Continued)

(58) Field of Classification Search
CPC ....... B08B 9/023; B08B 2209/02; E05B 1/00; E05B 1/0069; E05B 2047/0023;
(Continued)

(56) References Cited

U.S. PATENT DOCUMENTS 7,360,674 B2 4/2008 Sassoon
7,989,779 B1 8/2011 Ray
(Continued)

FOREIGN PATENT DOCUMENTS

CH 699581 3/2010
DE 202004017284 U1 6/2005
(Continued)

OTHER PUBLICATIONS

International Search Report and Written Opinion issued by the European Patent Office, dated Apr. 23, 2020, for International Patent Application No. PCT/EP2020/051690; 15 pages.
(Continued)

*Primary Examiner* — Randall E Chin
(74) *Attorney, Agent, or Firm* — Faegre Drinker Biddle & Reath LLP

(57) ABSTRACT

A device for cleaning a handle, including a handle including a gripping surface to be disinfected, an application member for applying a cleaning liquid to the gripping surface, and cleaning liquid supply element including at least one reservoir for receiving cleaning liquid and distributing it to the application member. The application member includes at least one buffer reserve arranged in contact with the gripping surface. The device includes a unit for actuating the application member, including drive element configured to move the buffer reserve and/or the gripping surface relatively with respect to one another so as to apply cleaning liquid to substantially the entire gripping surface during this movement.

23 Claims, 13 Drawing Sheets

(51) Int. Cl.

| | |
|---|---|
| *A61L 2/235* | (2006.01) |
| *A61L 2/24* | (2006.01) |
| *B08B 1/14* | (2024.01) |
| *B08B 1/30* | (2024.01) |
| *B08B 3/04* | (2006.01) |
| *B08B 9/023* | (2006.01) |
| *B08B 13/00* | (2006.01) |
| *E05B 47/00* | (2006.01) |
| *F03G 1/02* | (2006.01) |
| *H02K 7/18* | (2006.01) |
| *H02K 11/00* | (2016.01) |

(52) U.S. Cl.
CPC ............... *B08B 1/143* (2024.01); *B08B 1/30* (2024.01); *B08B 3/04* (2013.01); *B08B 9/023* (2013.01); *B08B 13/00* (2013.01); *E05B 1/00* (2013.01); *F03G 1/028* (2021.08); *H02K 7/1853* (2013.01); *H02K 11/0094* (2013.01); *A61L 2202/14* (2013.01); *A61L 2202/17* (2013.01); *B08B 2209/02* (2013.01); *E05B 2047/0023* (2013.01)

(58) Field of Classification Search
CPC ... A61L 2/18; A61L 2/24; A61L 2/235; A61L 2202/17
See application file for complete search history.

(56) References Cited

U.S. PATENT DOCUMENTS

| | | |
|---|---|---|
| 2005/0011042 A1 | 1/2005 | Hupp |
| 2010/0140499 A1 | 6/2010 | Casale |
| 2012/0176241 A1 | 7/2012 | Pasch |
| 2014/0137369 A1 | 5/2014 | Street |
| 2023/0212877 A1 | 7/2023 | Horvath et al. |

FOREIGN PATENT DOCUMENTS

| | | |
|---|---|---|
| DE | 102010011309 | 1/2014 |
| DE | 102013009098 | 5/2014 |
| EP | 0351307 | 1/1990 |
| EP | 1164234 | 12/2001 |
| EP | 1164235 A2 | 12/2001 |
| EP | 3118395 | 1/2017 |
| GB | 2141201 A | 12/1984 |
| GB | 2363075 A | 12/2001 |
| GB | 2433878 | 7/2007 |

OTHER PUBLICATIONS

English translation of the International Preliminary Report on Patentability issued by the International Searching Authority, dated Jul. 27, 2021, for International Patent Application No. PCT/EP2020/051690; 11 pages.

International Preliminary Report on Patentability received for PCT Patent Application No. PCT/EP2020/051690, mailed on Aug. 5, 2021, 20 pages. (9 pages of English Translation and 11 pages of Original Document).

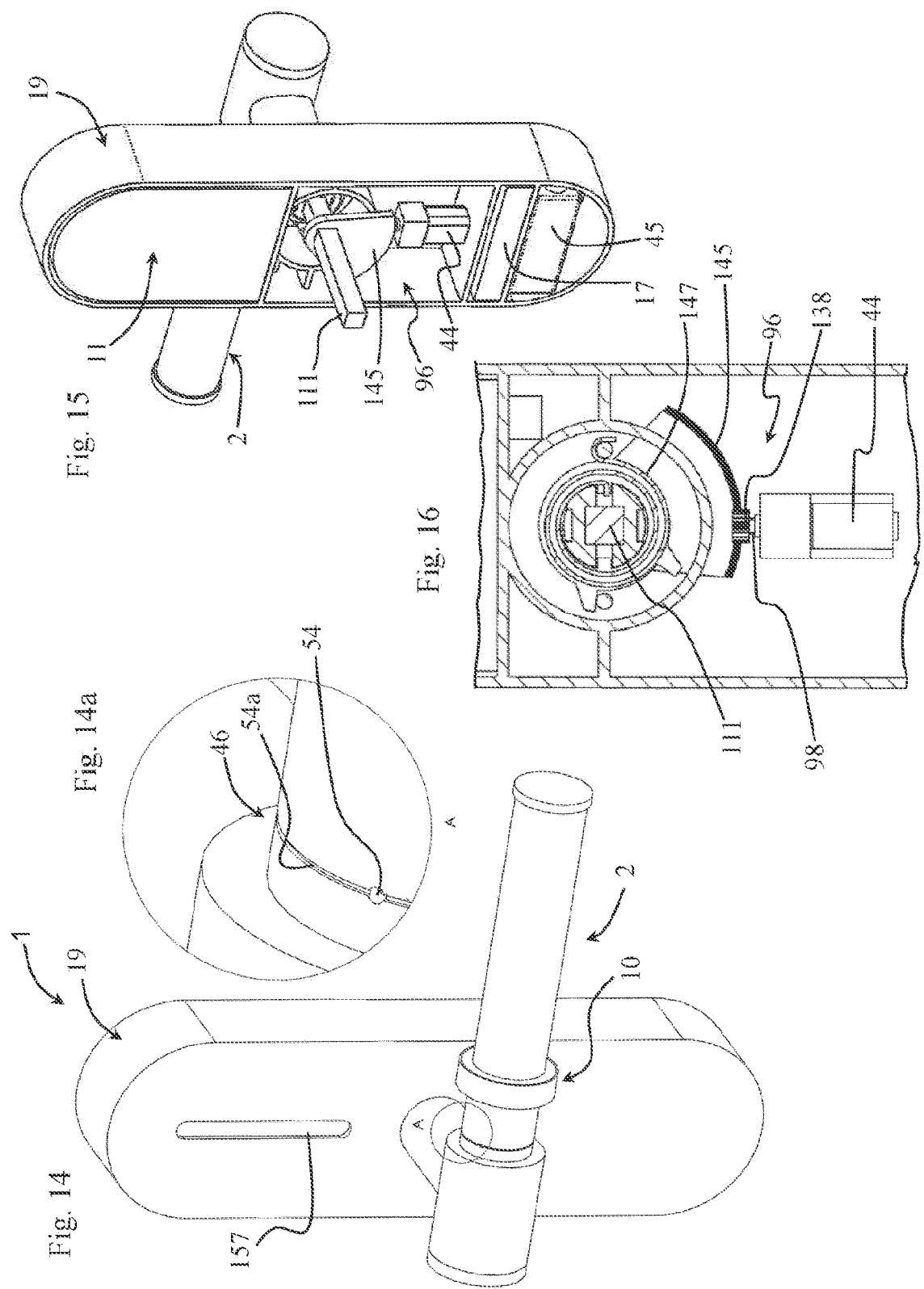

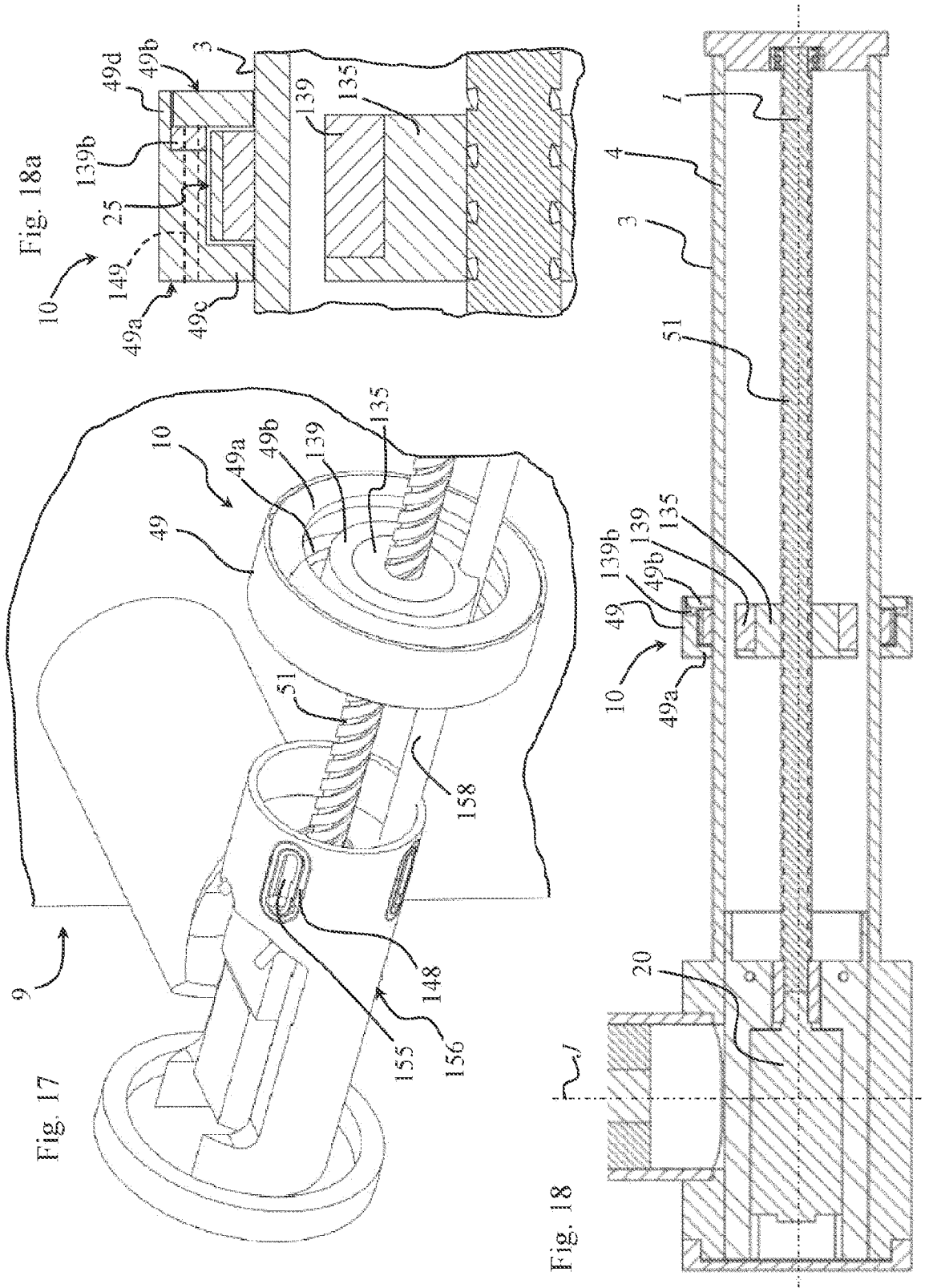

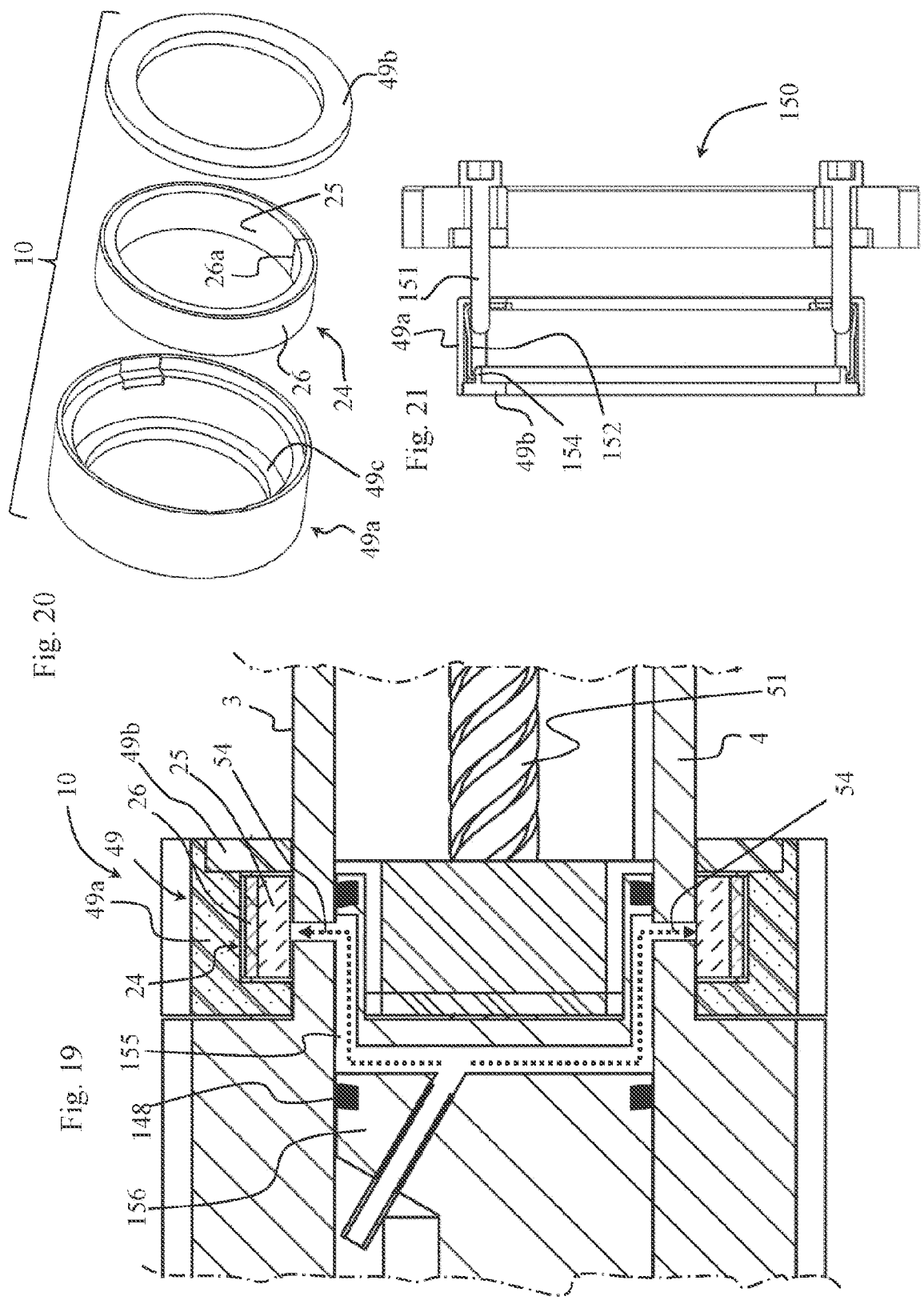

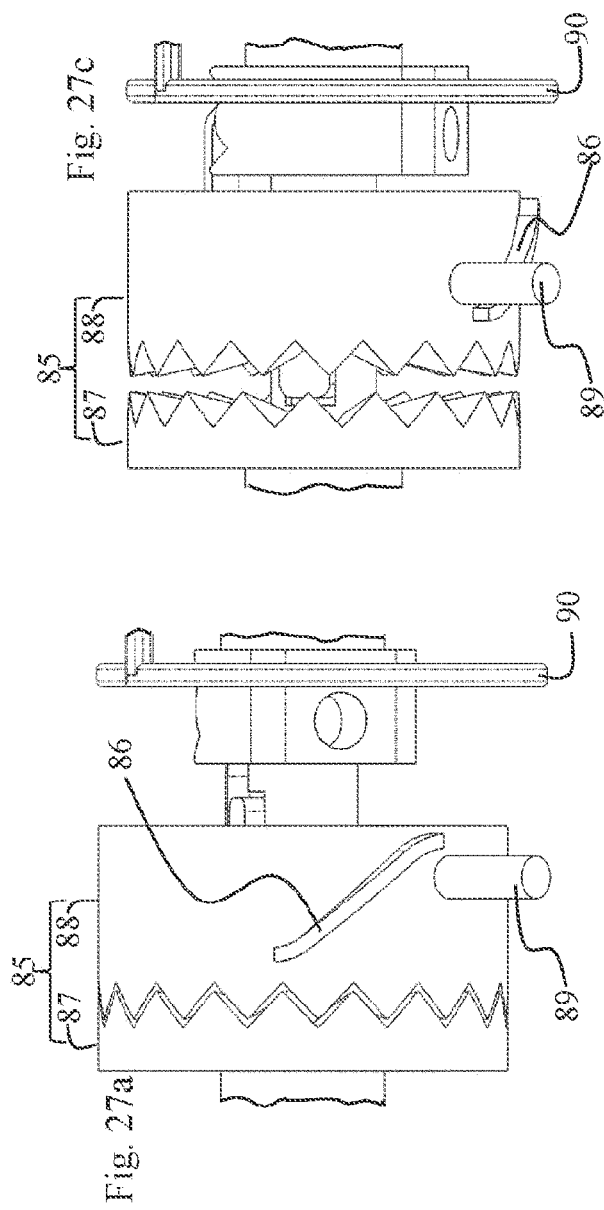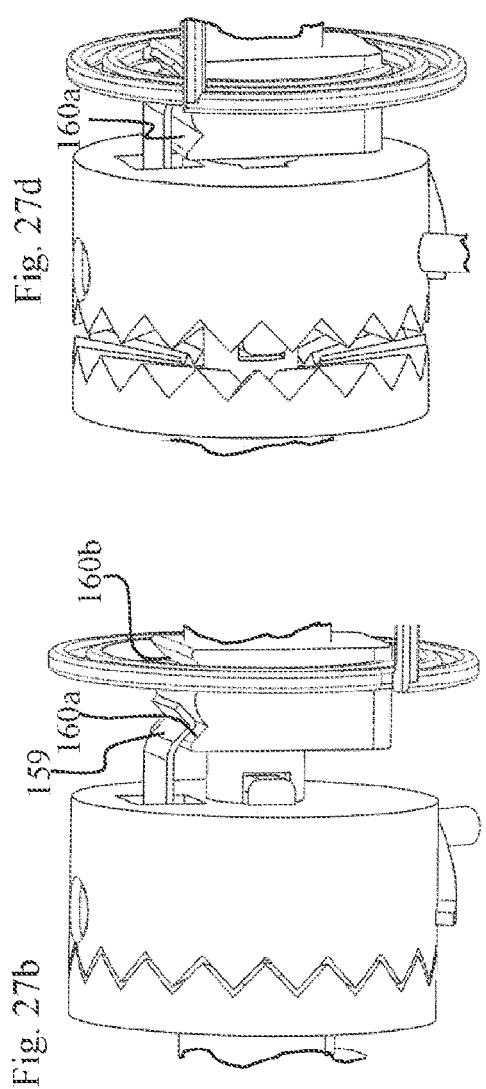

DEVICE FOR AUTOMATICALLY CLEANING A HANDLE

CROSS-REFERENCE TO RELATED APPLICATIONS

The present application is a divisional of U.S. patent application Ser. No. 17/425,265, filed Jul. 22, 2021, now U.S. Pat. No. 11,982,101, which is a national stage entry of International (PCT) Patent Application Number PCT/EP2020/051690, filed Jan. 23, 2020, which claims priority to European Patent Application Number 19153558.2, filed Jan. 24, 2019, the complete disclosures of which are expressly incorporated herein by reference.

The present invention relates to a device for automatically cleaning a handle, for example a handle for opening a leaf such as a door, a window, a French door or a handgrip or a handrail or a ramp.

In some high-traffic and/or sensitive public places, such as toilets, hospitals, operating suites, hotels, restaurants, shops, offices, etc., it is important to maintain good hygiene on the main contact surfaces to prevent the transmission of diseases. The handles have surfaces on which bacteria, viruses or other microorganisms are concentrated. A greasy deposit also builds up on these surfaces. It is therefore important and recommended to clean the handles regularly with a cleaning product preferably having disinfecting properties.

Thus, the cleaning of the surfaces such as handles is often carried out irregularly and incompletely. However, the transmission of microorganisms (viruses, bacteria, fungi, etc.) can be done easily and quickly by simple touch of an infected surface. It is therefore difficult to eliminate the risk of transmission by traditional cleaning methods.

Many systems for automatically cleaning handles are disclosed in the prior art, for example as described in the patent publications/patent applications U.S. Pat. No. 7,360,674, EP3118395, DE102010011309A1, US20100140499, U.S. Pat. No. 7,989,779, US20120176241, US20140137369, EP0351307, US20050011042, EP1164234, CH699581, and DE102013009098.

The handles can be heavily urged and their omnipresence results in that the users do not pay much attention or special care when using a handle. Handles with cleaning mechanisms must remain compact while being reliable and robust, requiring minimal maintenance as for a handle without a cleaning device. The autonomy and the low consumption of a cleaning product are also important. These various constraints are however difficult to gather and no existing system can achieve all the desired goals in a configuration that must also be inexpensive.

There is therefore a need to propose an efficient satisfactory solution for cleaning a handle, whose functionalities and ergonomics are maintained.

One object of the invention is to provide a device for cleaning a handle which is compact, efficient, reliable and inexpensive to install and use.

It is advantageous, for some applications, to provide a device for cleaning an energy-autonomous handle in its mode of operation.

Objects of the invention are achieved by a device for cleaning a handle according to the independent claims.

The dependent claims describe advantageous characteristics of the invention.

Hereby, a handle cleaning device is described, comprising at least one handle comprising a gripping surface to be cleaned, preferably forming part of a tubular or partially tubular-shaped wall, an application member for applying a cleaning liquid on the gripping surface, and cleaning liquid supply means comprising at least one tank for receiving and distributing cleaning liquid to the application member. The application member comprises at least one buffer reserve arranged in contact with the gripping surface and in that the device comprises a unit for actuating the application member comprising driving means configured to move the application member relative to the gripping surface and/or to move the gripping surface relative to the application member, so as to apply cleaning liquid from the buffer reserve on the gripping surface during this relative displacement.

One aspect of the invention is based on the principle of the relative mobility of a cleaning member on the contaminated surface and containing a reduced, preferably predosed, volume of liquid, according to the surface to be cleaned. Thus, the device is efficient, space-saving and its energy requirements to operate are low. The buffer reserve is preferably configured to contain a volume of cleaning liquid determined to clean the entire gripping surface during the relative displacement. Therefore, the cleaning is complete and reproducible at each cycle. The reloading of the buffer reserve by the activation of the liquid supply means can also be done in masked time, and not at the time of cleaning during the relative displacement of the application member against the surface to be treated. It is thus easier to monitor the dose of liquid needed to clean the surface. This results in a lower risk of a liquid supply fault during the cleaning step. Finally, this makes it possible, through collection means (described below), to use the energy produced by the mechanical actuation of the handle like during the opening of the leaf.

The gripping surface is not necessarily tubular and may be partially tubular in the sense that it may form a partially longitudinally open surface such as a U- or C-cross-shaped helical surface, or the like.

According to another possible configuration, the gripping surface could be for example formed of a series of several tubes of small diameters individually arranged in free rotation along their own individual axis and arranged together in a circular disposition about a longitudinal mid-axis of the handle thus forming a tubular or semi-tubular assembly of larger diameter.

The term "cleaning" relates primarily to a disinfection (that is to say, destruction of microorganisms or germs) and possibly degreasing operation. The term "cleaning liquid" relates primarily to a liquid having disinfecting and possibly degreasing properties. Preferably, the liquid consists of or contains a hydro-alcoholic solution and/or a solution containing surfactants or soaps capable of removing or dissolving greasy substances.

Preferably, the liquid supply means comprise a pump which can be actuated in an electronically or mechanically monitored manner by actuation of the handle. The pump may be a peristaltic pump or a piston pump or a pump of another type. In one possible arrangement, the pump is configured to supply the buffer reserve under the effect of a mechanical action applied on the pump by at least one element for actuating the handle associated with the movement of the rotating handle during the actuation of a mechanism for opening and/or closing the leaf.

According to one preferred aspect of the invention, the buffer reserve comprises an applicator pad in contact with the gripping surface having a structure allowing storing the liquid in a porous structure or a liquid retention interstice structure such as by capillarity effect. Such a configuration of the buffer reserve has the advantage of being able to better regulate the application and spreading of the liquid on the surface, while advantageously minimizing the risk of leaks.

It also has the advantage of providing a volume of liquid dimensioned to cover the entire gripping surface during a single cycle of relative displacement (gripping surface/application member) during cleaning.

The material of the applicator pad can be advantageously compressible. The compressibility also ensures better regularity in the application and reduces the risk of spots not covered by the liquid. The material can be: a sponge or a foam, a wire brush, a thickness or a fiber winding, a honeycomb structure, polymer balls or any material provided with a multitude of cavities or interstices of small volumes forming a network for regulating the liquid output flow and/or spreading. The liquid capacity of the buffer reserve depends on the gripping surface to be treated but may for example be comprised between 0.05 and 3 ml, preferably between 0.1 and 1 ml.

The transverse dimension of the applicator pad can be provided so that the applicator pad covers the entire surface to be treated during the relative displacement. The cleaning can thus be obtained depending on the case by a one-way displacement or in a single passage or by a two-way displacement or following a back and forth motion of the application member on the gripping surface or vice versa. In all cases, the displacement is preferably as short as possible and does not require complex movements or paths or trajectories.

According to one aspect of the invention, the device comprises a cleaning liquid distribution manifold comprising at least one liquid inlet in communication with the liquid tank and a plurality of liquid outlets distributed facing the buffer reserve, preferably the applicator pad of the application member. Thus, an arrangement with several liquid outlets allows distributing the liquid better and faster through the applicator pad, in particular over its entire width. This arrangement increases the efficiency of coating the treated surface, avoids the areas overloaded with liquid and also reduces the total volume of liquid required for a cleaning cycle.

According to one embodiment, the application member is at least in part an annular bushing mounted around the gripping surface, arranged to move axially along said surface between a distribution position in which the application member is opposite the distribution manifold, or in fluid communication therewith, for the transfer of cleaning liquid in the buffer reserve and an application configuration for the application of cleaning liquid on the gripping surface. Preferably, the application member comprises a rigid outer annular support inside which a ring-shaped applicator pad having an application surface in contact with the gripping surface is coaxially mounted. In this embodiment, the device remains ergonomic and the application member of the device is less cumbersome since it can be placed on one side of the handle, therefore without hindrance when the latter is operated in its gripping function.

In this case, the liquid distribution chamber of the application member preferably comprises a series of liquid outlets distributed over at least one circumference of the gripping surface in a transfer or reloading area; said outlets being arranged facing an annular portion of the applicator pad in the reloading or supply position.

In the case of an axial displacement of the application member opposite the gripping surface which remains static on the collar of the handle, the device is simplified. The applicator pad is separable from the liquid distribution manifold which may form part of the wall of the gripping surface and/or of the collar of the handle; which allows simplifying the application member and avoiding the fluid connection problems associated with the connection of movable parts. The static distribution manifold thus acts as a liquid reload station with a fixed defined position for the applicator pad; which can be placed in the rest and reload or supply position opposite the manifold before and/or after a cleaning cycle.

Particularly, the application member of the applicator pad can be moved axially along the gripping surface by means of a screw or belt driving means, an electromechanical-type non-contact gear. By way of example, this driving means comprises a worm screw extending longitudinally inside the tubular wall of the gripping surface of the handle and a secured nut movable along the worm screw and secured to the application member by a connection passing through an opening or a longitudinal groove through the wall of the gripping surface or with a magnetic coupling of the ring of the application member with the nut of the worm screw (therefore without necessary opening or groove) thus allowing the axial displacement of the application member when the worm screw is driven in rotation.

In another embodiment, in the case of a magnetic coupling, the ring of the application member can be driven by a linear motor capable of creating an electromagnetic field of displacement of the member along of the gripping surface.

The monitoring of the driving means and/or of the supply means can be made by means of an electric motor and/or in a mechanical manner. The electrical and/or mechanical energy can advantageously be a collected energy, at least partially, by the drive force applied by the user on the handle during the actuation of the handle on a mechanism for opening and/or closing the leaf controlled by the handle. Preferred embodiments will be described later.

According to one possible monitoring mode, the device according to the invention is controlled by means of an electronic controller such as a central unit which can be housed in the handle or outside as in a casing, a portion of the leaf or a framing. Thus, the actuation unit comprises an electronic controller configured to automatically control the action of the driving means for the relative displacement of the buffer reserve with the gripping surface and/or to control the liquid distribution by the supply means for filling with liquid the buffer reserve of the application member from the liquid tank. More particularly, the electronic controller controls the actuation of an electric motor of the driving means. The controller can sequentially or concomitantly monitor the liquid supply by actuation of the pump and the activation of the driving means in particular the electric motor.

According to one advantageous embodiment, the device comprises at least one sensor arranged to detect the presence of the touch of the handle by a user, said sensor being associated with the electronic controller which is configured to automatically actuate the liquid supply and/or driving means, in response to a detection information. The presence of at least one sensor thus allows activating the cleaning sequence according to a detection mode that can be preestablished by programming the controller, for example just after the detection of the presence of a hand on the handle by the sensor(s), or before a contact of a hand on the handle, by the detection of a control movement of the user. For example, after a detection of presence by the sensor(s), the controller is programmed to activate the driving means to perform the application of the liquid on the gripping surface.

The sensor can be a presence sensor or a force sensor with a capacitive, optical, piezoelectric, piezo-resistive or ultrasonic effect. For example, one or more sensors are positioned on or inside the gripping surface of the handle, in particular in the most exposed areas such as in the center and/or at a free end of the gripping surface or of the collar.

In one possible supply mode using a monitored electric pump, the pump can be activated following the detection by the sensor(s) for a predetermined time corresponding to the filling volume of the buffer reserve. The launching of the supply step can be optionally initiated at any time such as upon detection of the touch or after detection of the touch and/or after a predetermined time. The application step for its part can be launched only after detection and once the sensor no longer detects the touch or the presence on the surface or the collar.

In another embodiment, the device comprises a pump actuated by a mechanical actuation means which transmits a force resulting from a pivot movement of the handle actuated by the user, for example the lowering and/or the horizontal return of the handle, like during the opening and/or closing the leaf. The pump may be a peristaltic or piston type pump, for example. The mechanical actuation means can comprise at least a ramp or a cam means which acts on a peristaltic compression means or a piston of the pump under the effect of the rotational movement of the handle actuated by the drive force of the user as its lowering and/or its raising.

According to one advantageous aspect of the invention, the device is configured to be energy-autonomous. Preferably, mechanical energy from the actuation of the handle is used and stored in the form of electrical, mechanical energy or a combination of these two types of energy to be then used to actuate the pump and/or the actuation means for the relative displacement of the application member and/or of the gripping surface.

Thus, the device comprises at least one storage and reversing block or a member for recovering mechanical energy by torque transmission means due to the rotation of the handle on a mechanism for opening and/or closing a leaf (door, window, etc.), for the storage of this mechanical energy and/or an electrical energy transformation and storage member and finally a member for redistributing this stored mechanical or electrical energy to the actuation unit or to the driving means or to an assembly formed of a translation block and a coupling block which controls the displacement of the gripping surface or of the application member.

According to a first possible embodiment, the energy recovery member is of the electrical type. Particularly, the energy recovery member can comprise a generator for converting mechanical energy into electrical energy such as a dynamo, with or without a speed multiplier, associated with the torque transmission means and comprises an electrical energy accumulator such as at least one supercapacitor and/or a battery configured to store the electrical energy thus generated by the generator and make it available to supply the driving means and/or the electronic controller.

According to one preferred embodiment, the energy recovery and restoration member is of the mechanical type.

Particularly, the recovery member is a mechanical energy accumulation member, a mechanical energy restoration and transmission member or a storage and reversing block comprising at least one transmission mechanism with at least one shaft for transmitting a torque to a leaf closing mechanism, at least a first spring arranged to store the mechanical energy during the displacement of said shaft, a first one-way clutch and a set of cyclic latches actuated by a camshaft to restore the energy stored by the first spring to transmission and coupling means, or translation block and coupling block, configured to move the application member relative to the gripping surface in a first direction.

According to a preferred example, the application member is moved on the gripping surface from a supply position to an end-of-stroke position. In this case, the preferably annular-shaped application member preferably moves axially on the gripping surface as previously mentioned. According to another example, it is the gripping surface, for example of helical shape (as described in one embodiment of the present application) that is displaced in rotation opposite an application member in the form of a cleaning bar.

According to one example, the transmission and coupling means may comprise a translation block and a coupling block for moving the application member in translation on the gripping surface. The translation block can comprise an assembly formed by a worm screw and a nut for example or a belt and pulley assembly associated with a connection element associated with the coupling block.

The coupling block can form a direct coupling by a rod or the like with the application member. Alternatively, the coupling block can be a magnetic coupling member allowing transmitting the force of the translation block to the application member without a mechanical connection.

In addition, the mechanical energy accumulation member, the mechanical energy restoration and transmission member or storage and reversing block can comprise movement reversing means configured to move the application member relative to the gripping surface in a second direction opposite to the first direction.

According to one preferred example, these reversing means comprise a second cyclic clutch and a second spring configured to move the application member in the second direction, for example to return the application member from its end-of-stroke position to its supply position, said second clutch being arranged between the second spring and the first spring in order to freely drive the application member without stress of the first spring.

According to one aspect of the invention, the liquid supply means comprise at least one pump actuated in an electronically monitored manner by an electronic unit or a mechanically monitored manner by mechanical actuation means during the actuation of the handle, preferably the pivoting thereof about its actuation axis for the actuation of a leaf opening/closing mechanism. Preferably, the pump is a peristaltic pump or a piston pump.

According to one possible aspect of the invention, the liquid tank may be contained in a removable container connected by detachable connection means to at least one connection interface of the supply means. The connection interface can be contained in the bracket of the handle or in a casing secured to the leaf. The interface can be provided with complementary connection means communicating with the application member via at least one duct.

According to one advantageous embodiment, the tank of the liquid supply means is located above the handle, the delivery of a volume of liquid dispensed to the buffer reserve being made by the opening of a mechanically or electrically actuated valve to let the liquid pass only by the pressure due to the gravitational force.

According to one advantageous embodiment, the buffer reserve comprises an applicator pad in contact with the gripping surface detachably mounted in a rigid support of the bushing in order to be able to replace or clean the applicator pad.

According to one advantageous embodiment, the applicator pad is in the form of a flexible split ring so as to be able to pass the handle through an open slot of the split ring.

According to one advantageous embodiment, the rigid support of the bushing comprises at least two separable portions, the two portions being locked together by an elastic or magnet fixing mechanism, and unlockable with a tool comprising a pin.

According to one advantageous embodiment, the rigid support of the bushing comprises at least two separable portions, the two portions being locked together by a magnetic fixing mechanism.

According to one advantageous embodiment, the two portions of the rigid support of the bushing, comprise a base and a cover, the cover being housed in the base under an annular coating.

According to one embodiment, the device further comprises an unlocking tool comprising a magnet producing a magnetic field stronger than the magnetic field of the fixing mechanism.

According to one advantageous embodiment, the annular bushing of the application member comprises at least one permanent magnet housed in a rigid support of the bushing, the rigid support comprising or consisting of a ferromagnetic material.

According to one advantageous embodiment, the gripping surface comprises a circular groove intersecting distribution holes of the supply means for the irrigation of a buffer area corresponding to an initial position of the buffer reserve.

Other characteristics and advantages of the invention will emerge upon reading the following description, with reference to the appended figures, which illustrate:

FIG. 14 is a perspective view of a handle cleaning device according to one embodiment of the invention in a configuration in which it is being cleaned;

FIG. 14a is an enlarged view of the portion "A" of FIG. 14;

FIG. 15 is a perspective back view of the device of FIG. 14;

FIG. 16 is a sectional view of a portion of the device of FIG. 15;

FIG. 17 is a perspective view of a portion of a handle cleaning device, with a gripping tube removed to show the interior, according to one embodiment of the invention;

FIG. 18 is a sectional view of a handle of a handle cleaning device according to one embodiment of the invention;

FIG. 18a is an enlarged view of a portion of FIG. 18;

FIG. 19 is a sectional view of a portion of a handle of a handle cleaning device according to one embodiment of the invention, in the rest position;

FIG. 20 is an exploded perspective view of a liquid application member of a handle cleaning device according to one embodiment of the invention;

FIG. 21 is a sectional view of a liquid application member of a handle cleaning device and of a tool for opening the member, according to one embodiment of the invention;

FIGS. 27a to 27d are views of a detail of the cyclic clutch of the member of FIG. 24, in coupled (FIGS. 27a, 27b), respectively decoupled (FIGS. 27c, 27d) positions;

Figure 1:
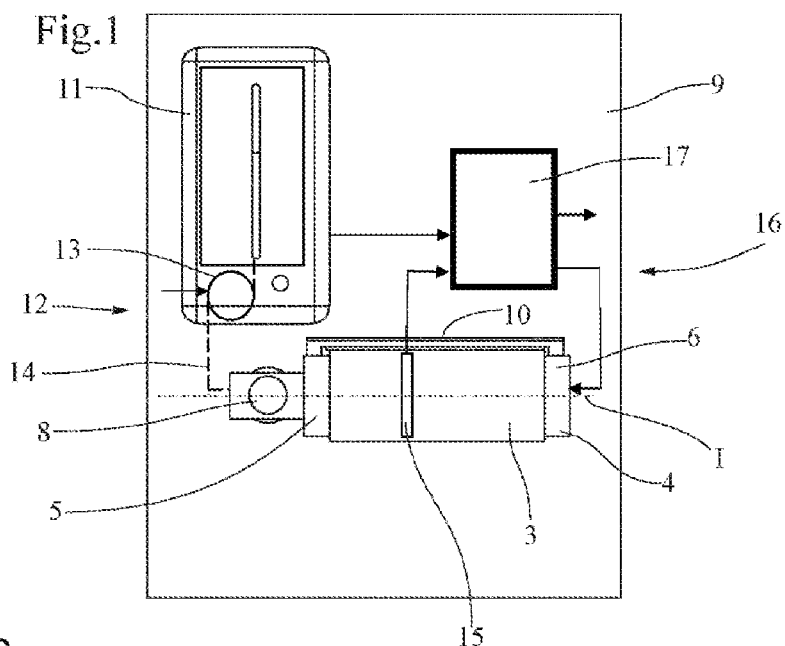
FIG. 1 is a general schematic front view of the handle cleaning device installed on a door according to one embodiment of the invention.
Figure 2:
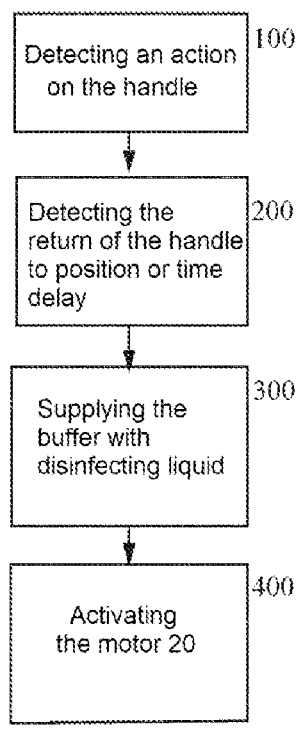
FIG. 2 is a flowchart of an example of a handle cleaning method according to the embodiment of the device of FIG. 1.

Referring to the figures, a cleaning device 1 comprises a handle 2 with a gripping surface 3 which may form the surface of a tubular-shaped or partially tubular-shaped wall and which extends along a median longitudinal main axis I.

A second handle identical to the handle 2 can be provided on the side opposite to the leaf 9. A second standard handle can be provided on the other side of the leaf 9. It should be noted that according to one possible embodiment, the handle can be fixedly mounted, without connection with an opening mechanism, on a door, window type leaf or on a panel, wall, floor or any other suitable support.

The device also comprises an application member 10 configured to apply a cleaning liquid on the gripping surface 3 and a liquid tank 11, containing a cleaning solution, of a capacity such that it allows for a multitude of cleaning cycles. Supply means 12 are provided to supply the application member 10 with liquid coming from the tank. These means 12 may comprise a liquid pump 13 as well as a line 14 connecting the tank to the application member 10.

An alternative method for irrigating the applicator pad 25 with disinfectant can be done by gravity, using a tank 11 located above the door handle 2. The monitoring of the dispensed liquid volume is made by the opening/closing of a mechanically or electrically actuated valve. For example, when the handle is in the rest position, the valve is closed, and when the door handle is engaged, a mechanism opens the valve to let liquid to pass only through the pressure due to the gravitational force.

The device may comprise at least one sensor 15 on the surface 3 for the detection of a hand presence or of the touch on the surface. The sensor 15 can be a presence sensor, for example of the capacitive type or an optical sensor such as an infrared sensor, or an ultrasonic sensor. The sensor can also be a force or pressure sensor such as a strain gauge or a piezoelectric sensor. The sensor can also be a movement or force sensor placed on the handle to detect a movement of the handle on its pivot axis such as its lowering during the opening of the leaf.

The sensor 15 can be configured for a movement detection, for example a sweep of the user's hand, in order to initiate a disinfection cycle. This feature allows the user to have a handle that can be disinfected before he touches it to have the visual confirmation that the disinfection has indeed taken place.

Other sensors can be provided such as a level sensor in the tank.

In general, the application member 10 is controlled by an actuation unit 16 comprising an electronic controller 17 and driving means 18 of the application member 10. The controller 17 can be housed in the handle itself as in the collar 4 or outside as in a casing integrated or associated with the support 9. The controller can also be present in the casing of the tank 11.

Figure 5:
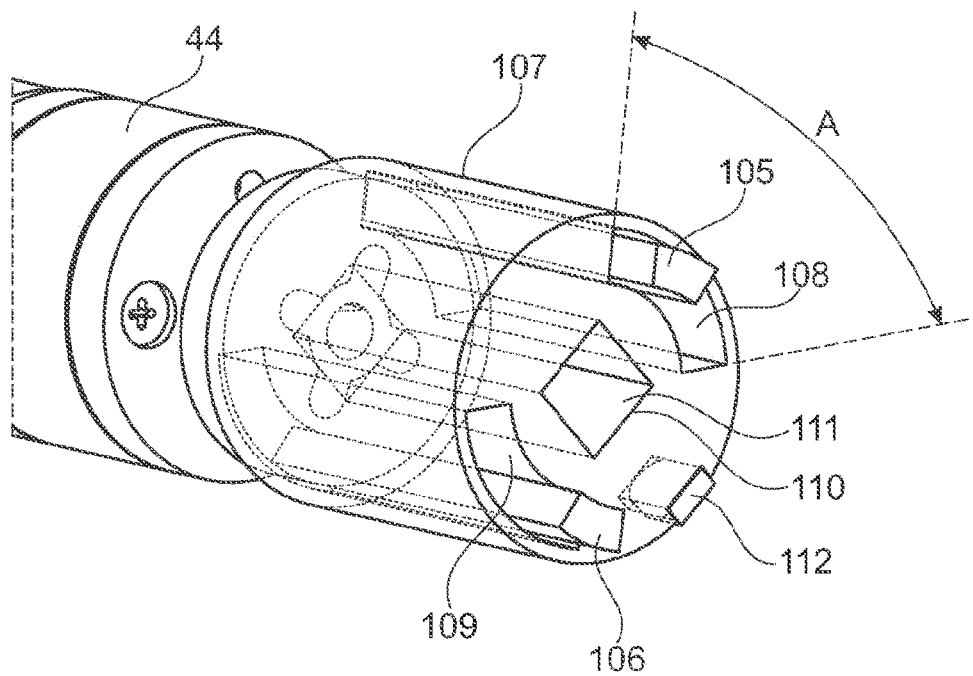
FIG. 5 is a partial perspective view showing a detail of the energy recovery member of FIG. 4, particularly, the means for transmitting the torque by the handle to the leaf.
Figure 6:
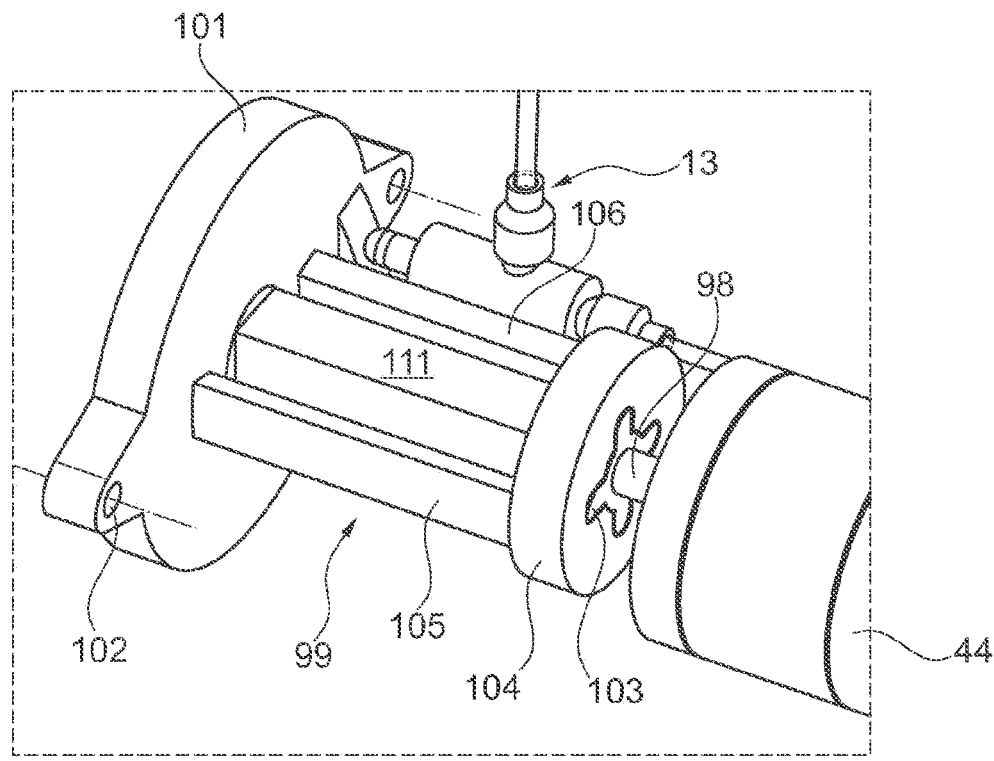
FIG. 6 is a partial perspective view showing another detail of the energy recovery member of FIG. 4 particularly the kinematic connection between the engine and the torque transmission means.
Figure 7:
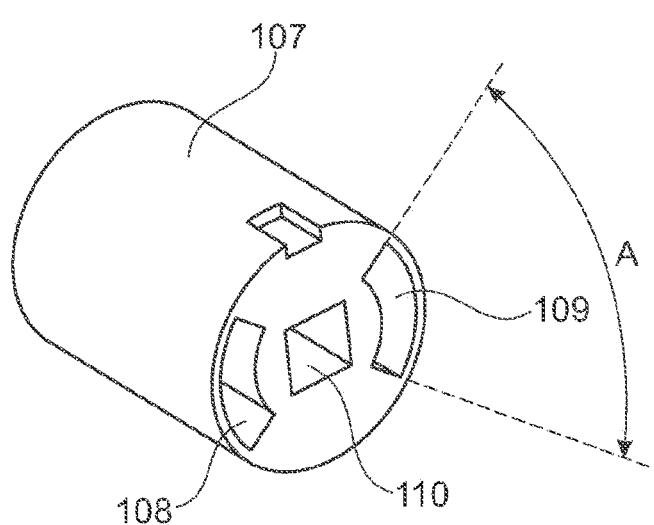
FIG. 7 shows an element of the torque transmission means of the device of FIGS. 4 to 6.
Figure 8:
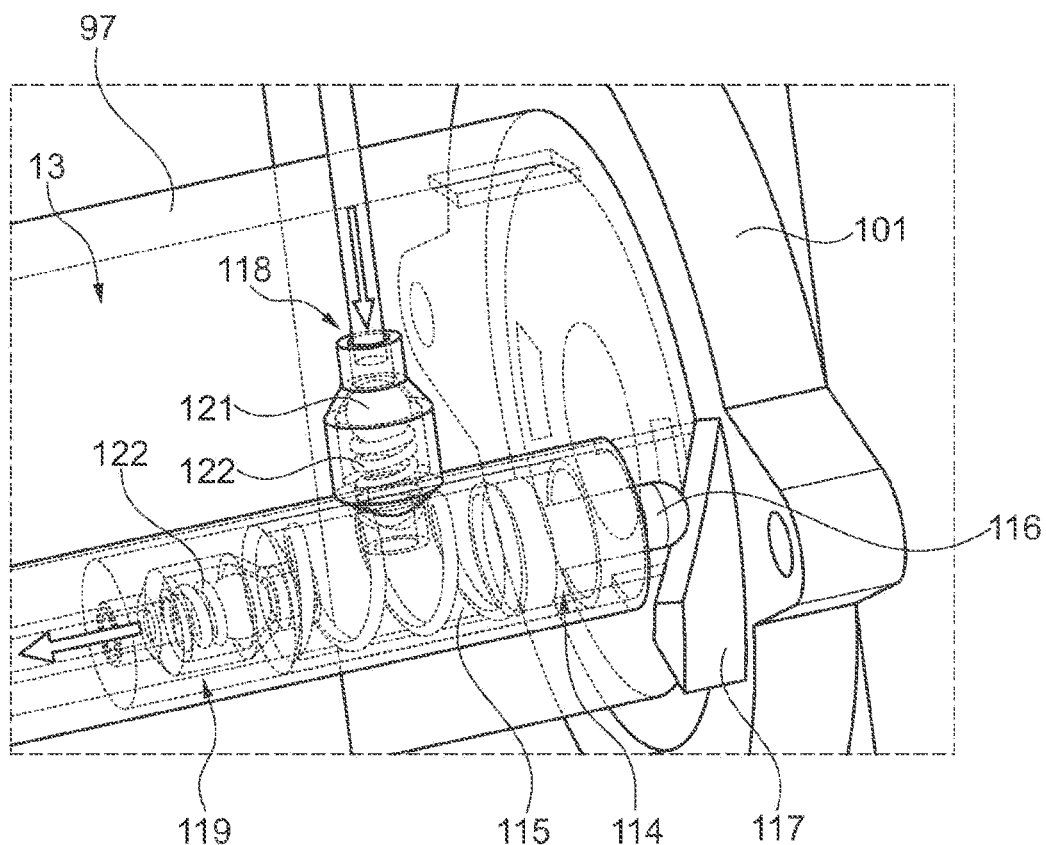
FIG. 8 shows a detail of the means for supplying with liquid the handle, particularly a piston pump, actuated by the movement of the handle during the actuation of a mechanism for opening and/or closing the leaf.
Figure 9:
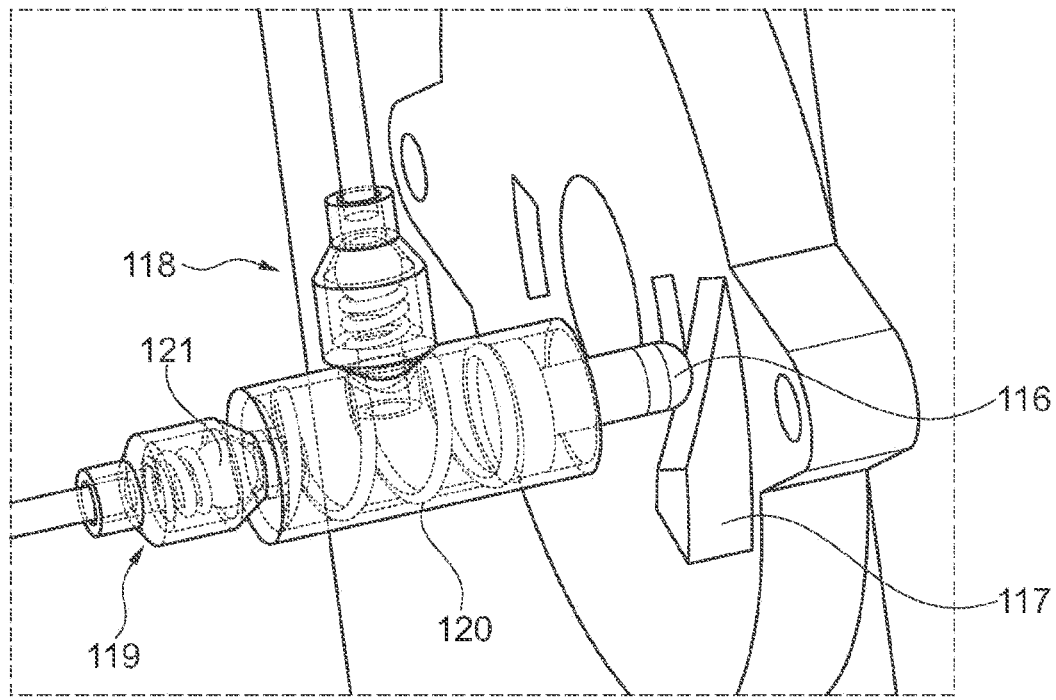
FIG. 9 shows a detail of means for supplying with liquid the handle without the bracket of the handle.

An example of operation of the device according to one possible embodiment can be explained in relation to FIG. 5. In a first step 100, an action on the handle is detected by the presence sensor(s) 15. This information is processed by the electronic controller 17. This step can be followed by a second step of detecting the stopping of the action on the handle 200 or the handle in the rest state. For that, the controller 17 receives the information from the sensor on the absence of presence. In this case, the controller initiates the next step 300 consisting of supplying the buffer reserve 24 with cleaning liquid by activation of the pump 13. According to one possible alternative embodiment, the second step 200 consists of applying a time delay following the detection step 100 before initiating the next step 300. According to one possible alternative embodiment, the actuation of the pump and/or of the application member can be done by mechanical actuation means by the mechanical action of the handle displacement, by rotation or other movement, to control the opening and/or closing of the leaf. An optional step of checking the liquid level can be implemented in order to check the capacity of the tank to fill the reserve buffer. If the liquid level is insufficient, the method can be interrupted and a recharge signal emitted by the controller 17. During the following step 400, the controller activates the driving means 18, particularly the electric motor 20, to drive the application member. The translation has the effect of applying the liquid of the applicator pad and distributing its volume on the gripping surface. The liquid layer may be calibrated by a calibration means preferably by a restriction such as a calibrated slot and/or a transverse lip disposed between the buffer reserve and the surface (not illustrated).

Once the translation is completed, the controller 17 orders the stopping of the driving means 18. The displacement can be monitored by any means such as by an encoder, by an electrical measurement such as the power consumption of the motor or by a time delay. It should also be noted that the supply step can be implemented between the two first detection steps 100, 200 or after the last actuation step 400.

Figure 3:
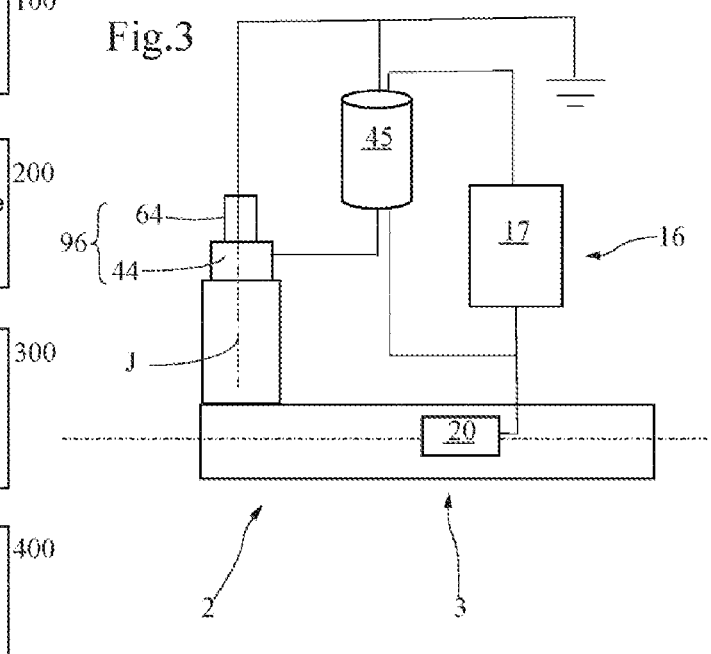
FIG. 3 is a schematic illustration of an electrical energy recovery member of the device.
Figure 4:
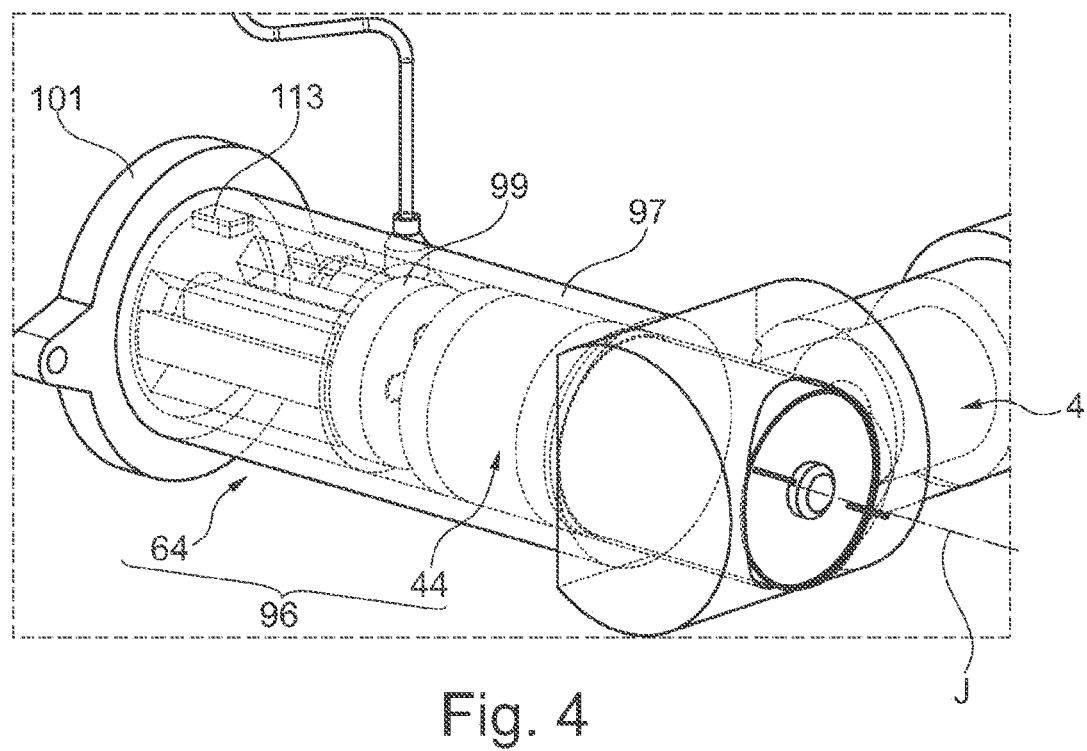
FIG. 4 is a perspective view in transparency of a portion of the handle comprising a portion of the energy recovery member of FIG. 3.

FIG. 3 illustrates a general principle of electrical energy recovery by an energy recovery member 96 to supply the electrical components of the handle including the actuation unit 16. Thus, the device comprises a generator for converting mechanical energy into electrical energy 44. The generator is connected to a torque transmission mechanism 64 connected to the leaf closing mechanism which transmits the mechanical energy to the generator when the handle is manually actuated pivotally about an actuation axis J. The generator 44 can be a motor, a geared motor or a dynamo. The device also comprises at least one electrical energy accumulator 45 electrically connected to the generator to store the thus produced electrical energy. Such an accumulator can be a (super) capacitor and/or a rechargeable battery configured to store the thus generated electrical energy. The accumulator is electrically connected to the actuation unit 16 to supply the driving means and the electronic controller 17.

FIGS. 4 to 7 illustrate a first example of an energy recovery member 96 operating based on the general principle of FIG. 3. Thus, the member comprises an electric generator 44, such as a dynamo, housed inside a tubular bracket 97 of the handle which is connected to the gripping collar 4 in a rigid manner to form an elbow for example. The electric motor 44 is inserted into the bracket in a fixed manner along the longitudinal axis J of the bracket corresponding to the pivoting axis of the handle and comprises a transmission shaft 98 which is secured to a collar 99 configured to be fixed on a wall of the leaf (not represented). The collar can be fixed to the leaf more particularly by a flange 101 of the collar 99. The flange 101 may have the form of a disc or the like provided with holes 102 allowing the fixing to the leaf by means of screws, rivets or the like. The shaft 98 of the motor can be connected for example by a connecting part 103 to a proximal end 104 of the collar 99. The collar comprises transmission bars, for example two parallel bars 105, 106, which connect the proximal end 104 to the distal end formed by the flange 101. The torque transmission member further comprises a cylinder 107 disposed between the ends 101, 104 of the collar 99, provided with through slots 108, 109 for the sliding passage of the transmission bars 105, 106. The slots are dimensioned in the form of arcuate openings in the circumferential direction of the cylinder and of angle A corresponding to the angle of pivotal displacement of the handle along the axis J during the opening/closing movement of the leaf mechanism. For example, the angle can be from 25 to 60 degrees. The cylinder 107 comprises a central through-bore 110 in the axis J of non-circular, for example square, cross-section in order to receive a side rail 111 of section complementary to the section of the bore, which is intended to pass through the leaf to transmit the torque of the manual actuation of the handle on a mechanism for opening/closing the leaf. The cylinder comprises rotational blocking means for blocking the cylinder opposite the bracket. These blocking means can comprise a key 112 configured to engage in a housing 113 of the bracket of the handle in order to secure the cylinder with the bracket during the pivoting of the latter during the actuation of the handle.

The operation of the energy recovery member 96 is as follows. When a user lowers the handle, the tubular bracket 97 secured to the gripping collar 4 pivots about the axis J by an angle A, for example 30 degrees. The shaft of the motor secured to the collar 99 itself secured to the leaf remains stationary while the motor itself secured to the bracket rotates with the bracket by 30 degrees about the axis J. This movement induces an electric current in the motor which is collected by the electric accumulator. The repetition of the opening and/or closing cycles allows charging the accumulator and supplying the electric motor of the actuation means. The torque of the mechanical action on the handle is transmitted by the bracket to the cylinder through the key 112 and from the cylinder to the side rail 111 to the mechanism of the leaf. The slots 108, 109 allow the rotational movement without deformation of the cylinder relative to the fixed collar. It goes without saying that other execution modes are possible, such as mechanical inversion in the example illustrated such as a rotatably movable generator in the bracket and a shaft secured to the bracket.

FIGS. 15 and 16 illustrate a second example of energy recovery member 96. The member comprises an electric generator 44, such as a dynamo, connected to an electrical energy accumulator 45, such as a rechargeable battery, housed inside the handle casing 19. The shaft 98 of the motor comprises a pinion 138 engaging a gear 145, for example in the form of a toothed disc portion, coupled to the side rail 111 to transmit the torque of the manual actuation of the handle on the pinion 138. This gear transmits and amplifies the movement to the small-diameter pinion. The electric generator may include a reduction gear in order to increase the transmission ratio between the rotation of the side rail 111 and the magnetized rotor of the generator. A return spring 147 returns the handle from its lowered position to its rest position. In one embodiment, the electric generator 44 is configured to charge the electrical energy accumulator 45 in both directions of rotation, however it is also possible to have the pinion 138 freewheeling in the return direction of the handle to its rest position.

The system can thus be made energy-autonomous by collecting the mechanical energy of the actuation of the door handle provided by the user and converting it into electrical energy.

An electronic module comprising the electronic controller 17 can also be housed in the handle casing 19, used for the monitoring of the motor of the application member, and/or for other functions of monitoring the system, comprising the display of the state of the system or the emission of alarms. In the case of a mechanical disinfection system, it is also possible to envisage a small collection of energy to supply the electronic module or other electronic components used for the monitoring of the system or the state display.

The means for supplying liquid to the cleaning device of the invention according to this embodiment can also comprise a pump 13 secured to the bracket 97 and actuated by the effect of the pivoting of the bracket 97 about the axis J during the actuation of the handle. For that, the pump 13 may comprise a piston 114 housed in a chamber 115 of the pump actuated in axial displacement by a finger 116 arranged in contact with an inclined plane or ramp secured to a fixed portion of the handle, for example of the flange 101. The pump preferably comprises an elastic return means for the piston such as a spring 120 in the chamber. The pump may comprise an intake check valve 118 in communication with the liquid tank by means of a duct portion and a discharge check valve 119 connected to a line portion supplying the application member. The valves can each be a ball valve 121 or needle valve comprising an elastic return means such as a coil spring 122 or any other type of one-way valve. The inclined plane 117 is configured relative to the pump so as to act on the axial position of the finger and therefore of the piston in the chamber. In the rest position of the finger, the piston compresses the liquid in the chamber and the liquid is discharged towards the application member. The discharge valve 119 is then opening-compressed to let the liquid pass. The inlet valve mounted in the opposite direction to the discharge valve is then closed by the return action of the spring on the ball. In the return position of the finger, the piston is in the expanded position in the chamber. The intake valve is opened by the pressure difference created between the chamber and the inlet line; which causes the liquid suction into the chamber and the filling thereof. The discharge valve remains closed by the elastic return of the spring 122 on the ball 121.

Figure 10:
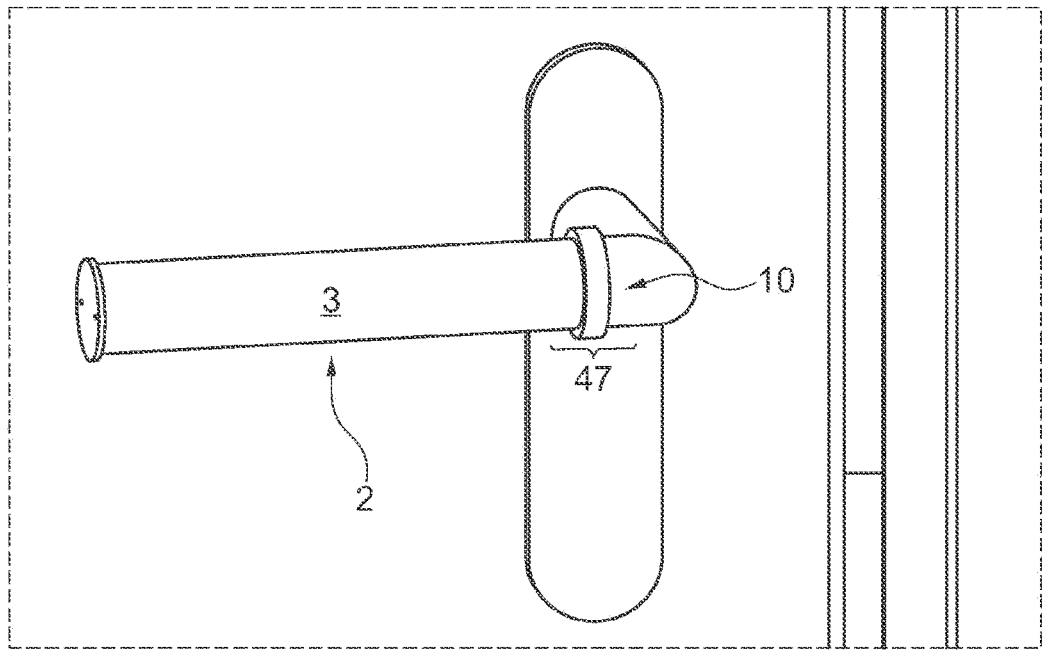
FIG. 10 is a general perspective view of a handle cleaning device installed on a leaf according to one embodiment of the invention in a liquid supply or rest configuration.
Figure 11:
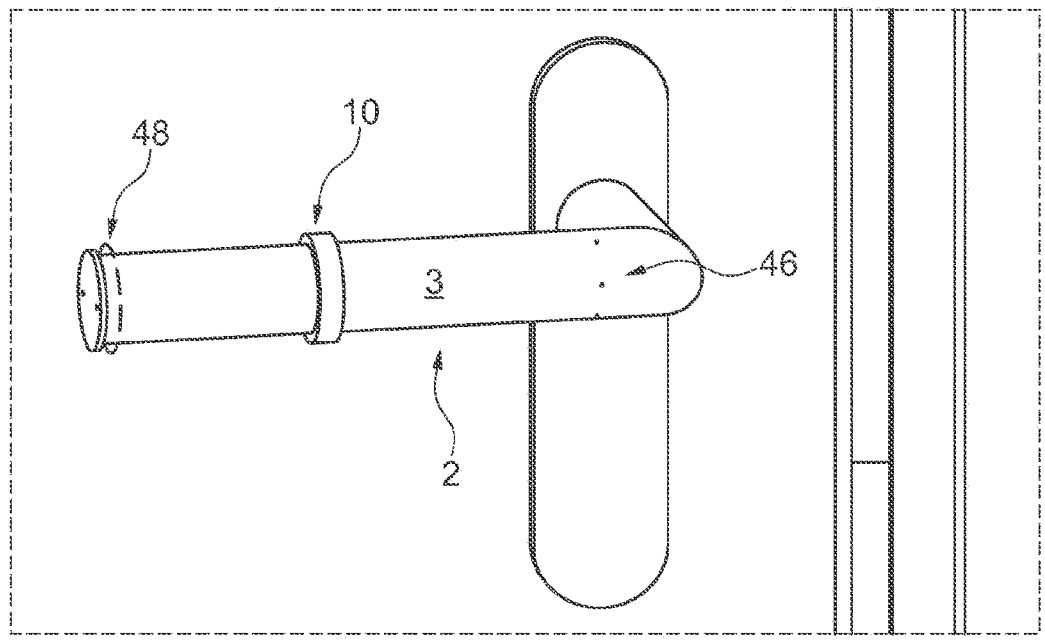
FIG. 11 is a general perspective view of the embodiment of FIG. 10 in a cleaning configuration.
Figure 12:
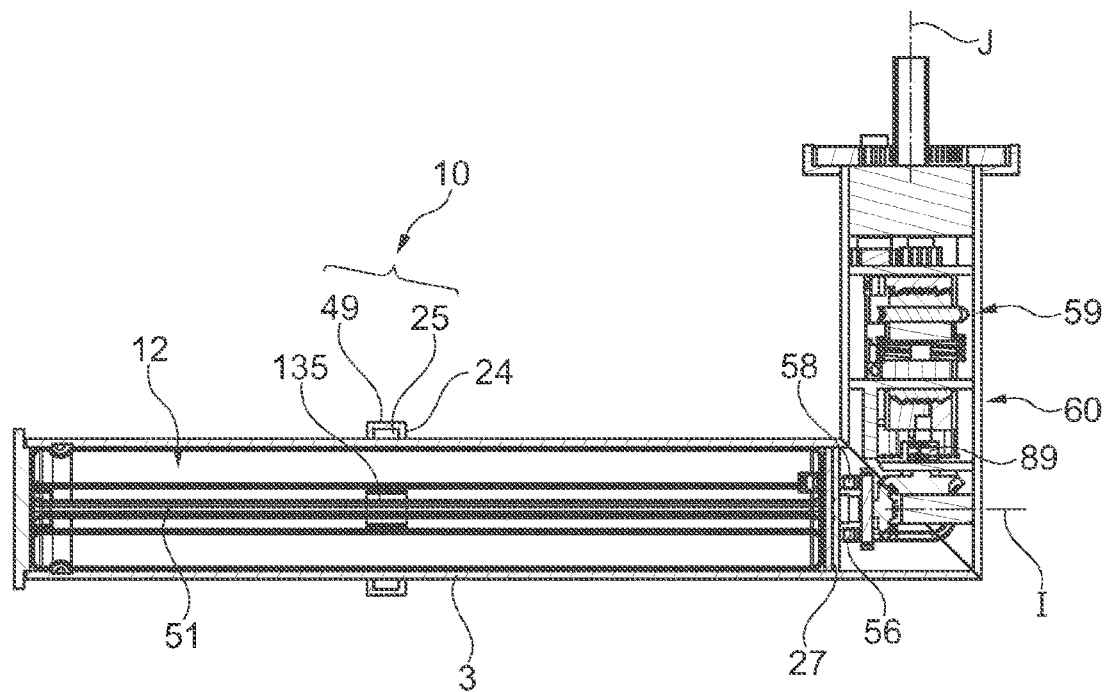
FIG. 12 is a sectional view along a median horizontal plane of the cleaning device according to one embodiment.
Figure 13:
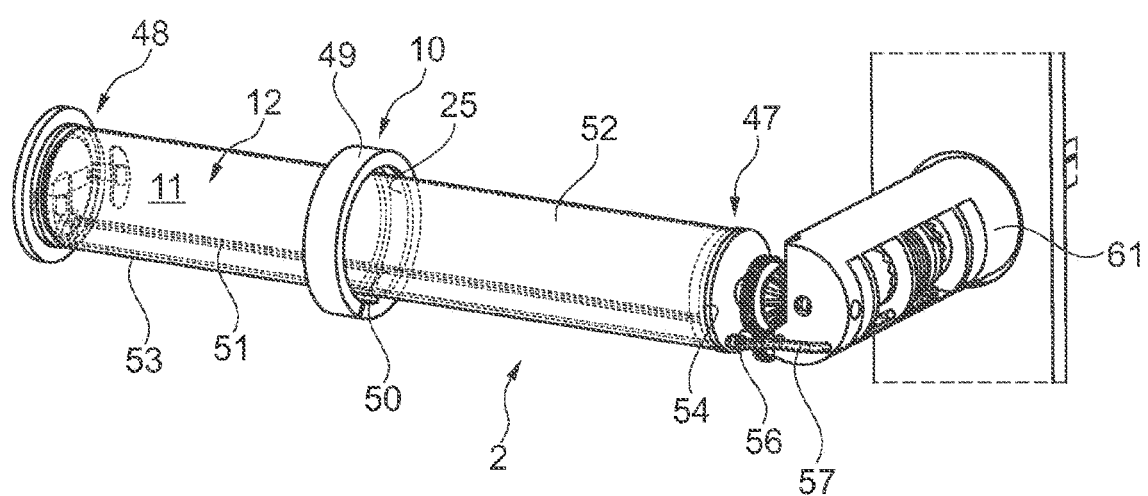
FIG. 13 is a perspective view without its complete external trim, particularly the coating of the handle by the tubular gripping wall of the embodiment of FIG. 12.
Figure 22:
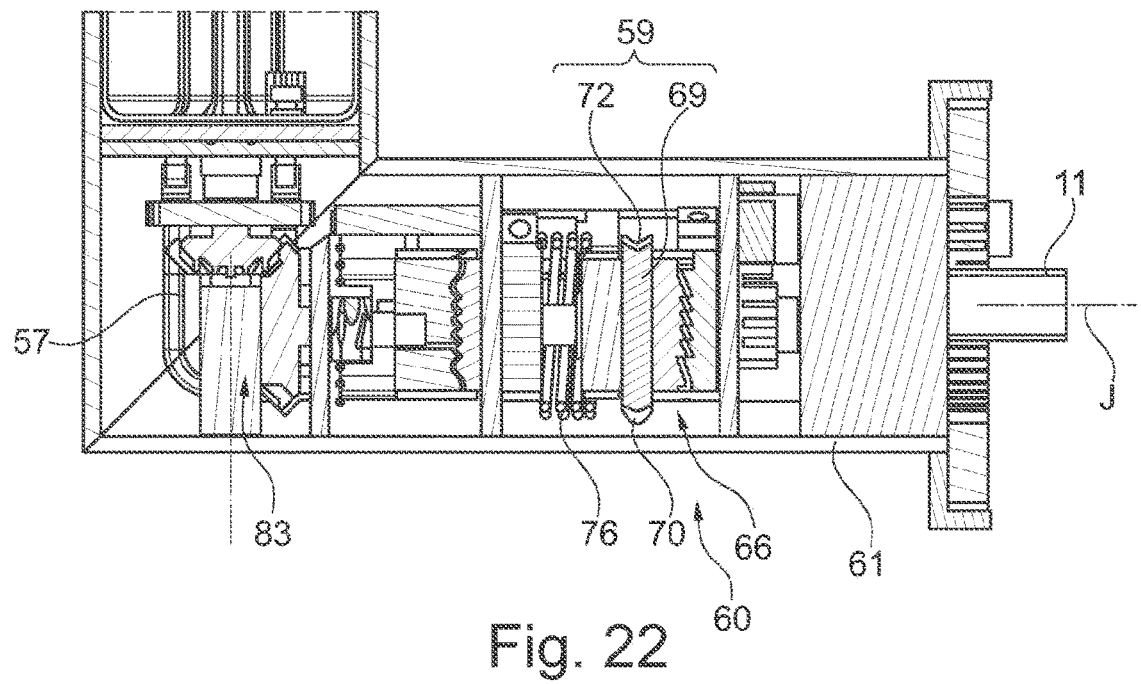
FIG. 22 is an enlarged view of a detail of the device of FIG. 12 particularly of the energy drive, recovery and restoration mechanism of the device ("Driving and energy member")
Figure 23:
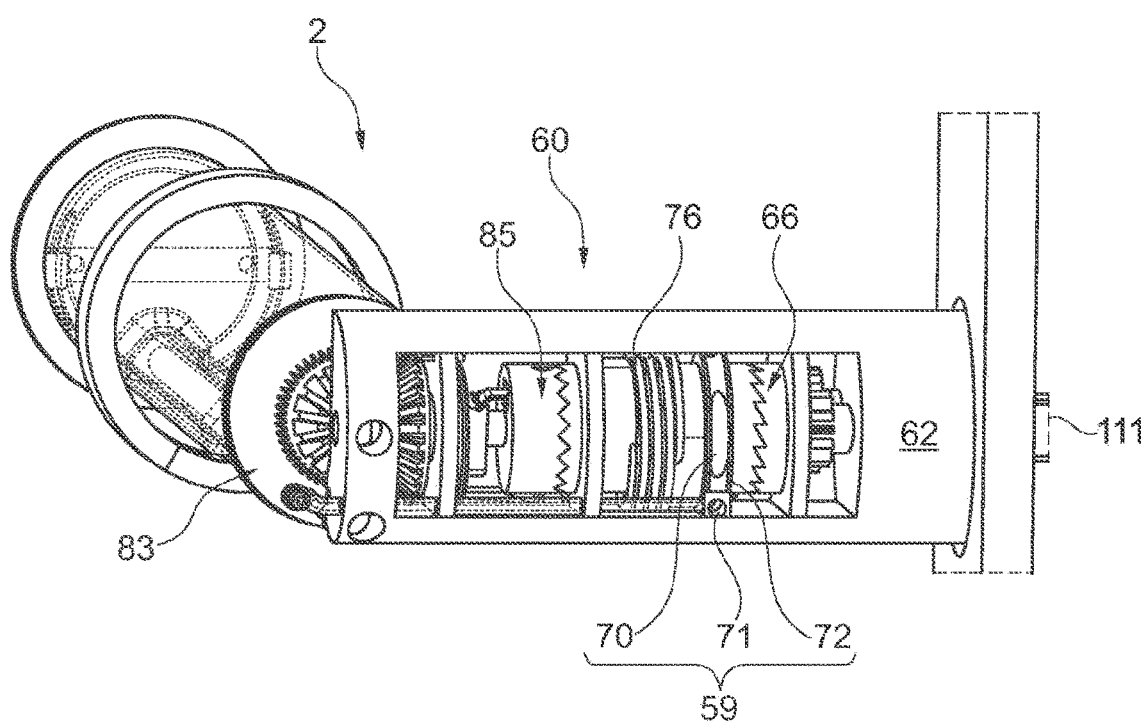
FIG. 23 is another external perspective view of the device of FIG. 12 showing the mechanical energy drive, recovery and restoration the member of the device.
Figure 24:
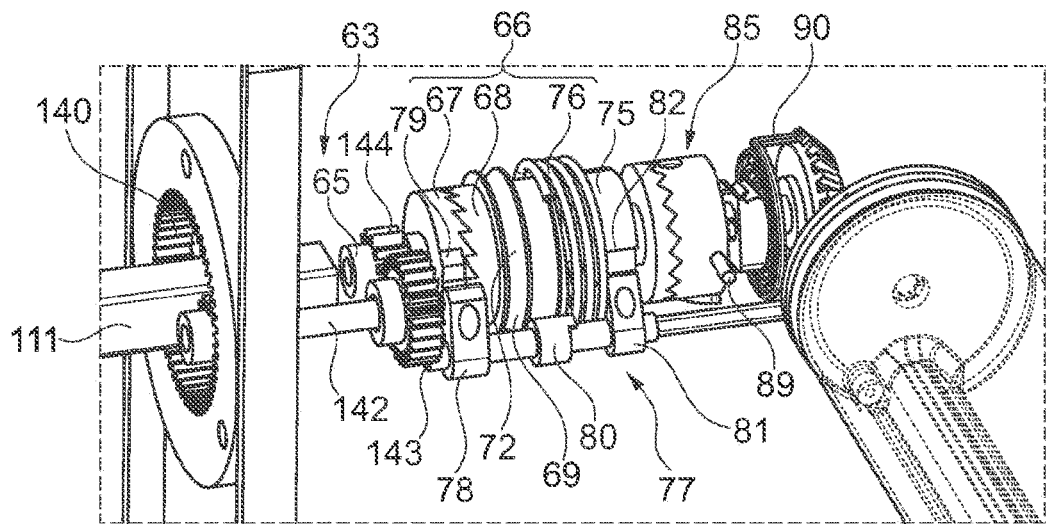
FIG. 24 is a view from another angle of the energy and driving member of the device of FIG. 12.
Figure 25:
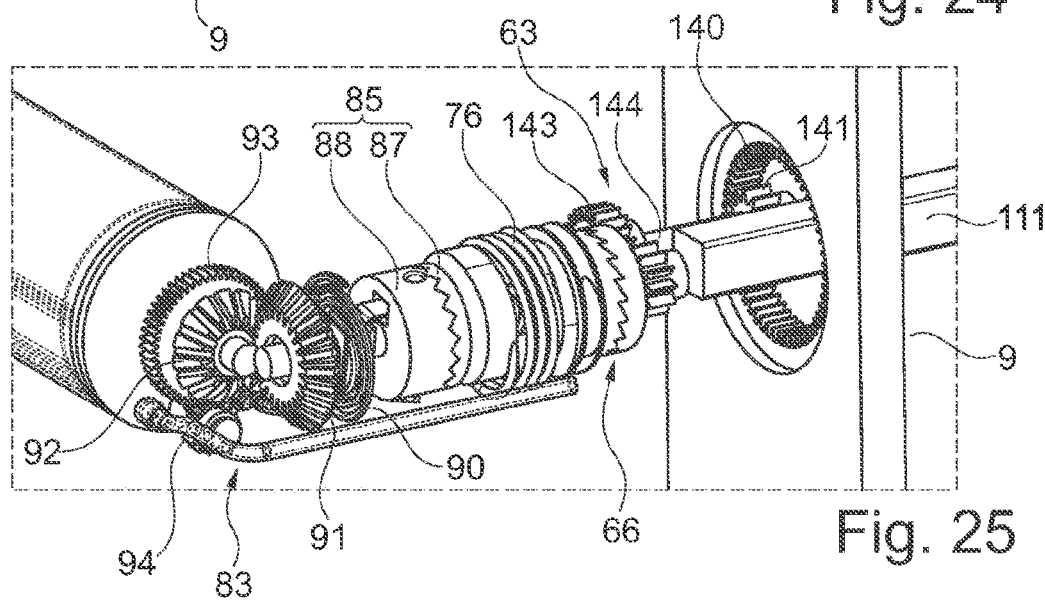
FIG. 25 is a view without the frame from another angle of the handle energy and driving member.
Figure 26:
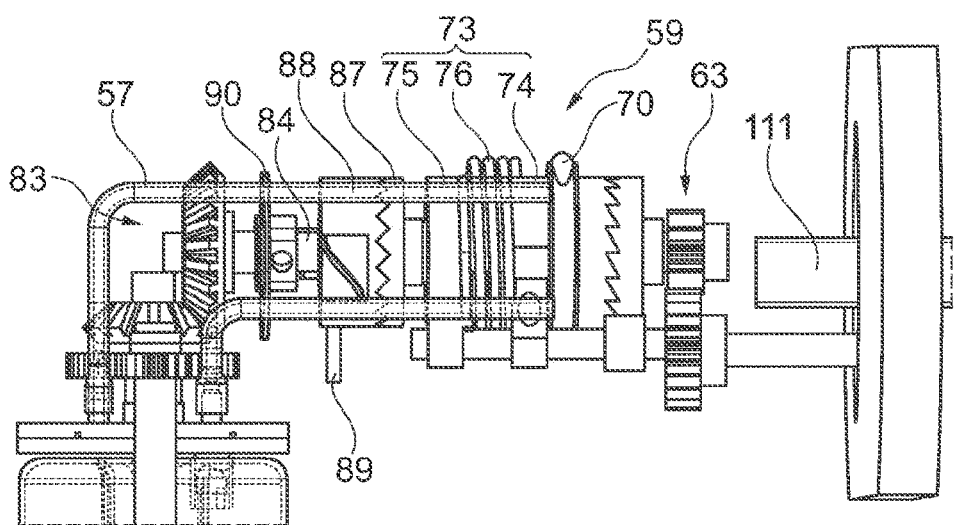
FIG. 26 is an enlarged detail view of the member of FIG. 24.

One preferred embodiment of the device according to the invention is illustrated in relation to FIGS. 10 to 27. In this embodiment, the handle 2 comprises a static gripping surface 3 and an application member 10 which moves longitudinally or axially (i.e. in the I-axis direction) along the surface during the cleaning. In particular, the application member 10 has the form of a bushing mounted around the surface 3 from a supply position in which the bushing covers a supply area 46 of the handle for the supply of the liquid into the member as shown in FIG. 10. The supply member is moved by actuation means which will be detailed later along the gripping surface 3 as shown in FIG. 11. The displacement can be done between the supply position 47 (FIG. 10) and an end-of-stroke position 48 corresponding to the end of the gripping surface (FIG. 11: position identified in dotted line). Once this end-of-stroke position has been reached by the application member, the latter is returned to the supply position to be reloaded with cleaning liquid by actuation means which will be described below.

As shown in FIGS. 12 and 13 and 18 to 21, the application member 10 comprises an applicator pad 25 disposed on the inner surface of a rigid annular support 49 of the member. The applicator pad 25 is disposed so as to remain in permanent contact with the gripping surface 3 during the axial displacement of the application member.

In one advantageous embodiment, the applicator pad 25 of the application member 10 is mounted in the rigid support 49 in a detachable manner such that it can be replaced or cleaned. Preferably, the application member 10 is arranged so as to be able to remove the applicator pad 25 from the handle while leaving the rigid support 49 on the handle.

Use after use, the applicator pad 25 becomes loaded with impurities (dust, greasy film left by the user's hand, etc.). In order for the disinfection function to continue to be performed efficiently, it is advantageous to regularly replace this buffer component by maintenance personnel. Therefore, a system allowing easy and quick access to the buffer component is necessary to facilitate the task for maintenance personnel. In addition, a locking system is advantageous for this purpose to prevent the component from getting lost or being stolen.

The rigid support 49 can be in two portions 49a, 49b, for example comprising a base 49a and a cover 49b mounted in a separable manner from the base. The applicator pad is locked in a radial groove of the rigid support formed between a flange 49c of the base 49a and the cover 49b. The cover can be fixed to the base in various ways. In the illustrated embodiment, the cover is locked to the base by an elastic fixing mechanism 152, 154. In the illustrated variant, the mechanism comprises an elastic arm 152 in the base 49a engaging a complementary shoulder 154 on the cover. It is also possible to have an elastic arm on the cover engaging a shoulder on the base. An unlocking tool 150 comprises a pin 151 insertable into the rigid annular support to disengage the elastic arm from the complementary shoulder.

In one variant (not illustrated), the two portions 49a, 49b of the ring 49 are screwed together.

In one variant, the two portions 49a, 49b of the ring 49 are assembled with one or more permanent magnets 139b, for example located in the shoulder of the base 49a, the cover 49b in the form of a washer being housed into a radial coating 49d. The coating 49d extends completely around the cover, which makes the separation of the two portions 49a, 49b by hand almost impossible since the user has no grip area on the cover. A tool 150 with a pin 151 can be used to push, through one or more holes 149, the cover 49b, while the base is being held, for example by the hand of the maintenance technician. In one variant, a tool with a permanent magnet generating a magnetic force greater than the magnetic force of the magnet 139b, can be used to detach the cover 49b from the base 49a.

The applicator pad may be in the form of a flexible split ring 26 so that it can be opened by spreading the ends of the slot 26a and so as to be able to pass the handle through the open slot. The applicator pad 25 can be arranged to exert a small elastic compression around the gripping tube 3 to compress the buffer material homogeneously on the gripping surface and allow good spreading of the disinfectant.

In one variant, the applicator pad can be in two portions, for example two halves.

The applicator pad can have various configurations, for example formed of a single piece, or formed of a rigid but flexible annular support 25a supporting a felt, foam or other application material 25b disposed on the radially internal surface of the flexible ring. A strip consisting of a buffer material 25b (such as felt, sponge etc.) can be bonded on the internal periphery of an elastic support material ring, for example made of plastic, to be in contact with the gripping tube. The role of this strip, firstly, is to be soaked with disinfecting liquid during the irrigation process. Secondly, the soaked liquid is distributed along the gripping tube during the translation of the ring.

Optionally, a second strip (not illustrated) can be bonded inside the support ring, axially to the buffer strip with a small spacing. This second strip acts as a scraper allowing recovering the surplus of disinfectant deposited on the gripping tube. This allows preventing a user from touching a wet handle, which can be perceived as unpleasant and at the same time preventing people with particularly sensitive skin from being in contact with the disinfecting liquid. This strip can be a sponge, felt, polymer or rubber type material.

In one embodiment, the annular support 49 is connected to the handle by a base 50 comprising a nut 135 which is mounted and moved on a worm screw 51 housed inside the partially tubular wall 52 of the handle and extending at least over the width of the gripping surface 3. The wall 52 comprises a longitudinal through-passage 53 extending axially to allow the base of the annular support of the member to move longitudinally in the passage between the supply position 47 and end-of-stroke position 48.

A liquid distribution manifold 27 is disposed in the supply position 47, it is configured with several liquid outlets 54 distributed radially and preferably substantially aligned in a circumferential plane of the gripping surface 3 so as to be covered with the applicator pad 25 when the application member is in the supply position. The distribution manifold 27 is preferably supplied by a connector 56 connected to a duct 57 which is connected to a liquid tank 11.

In one embodiment, liquid outlets 155 of the inner structure 156 are aligned with radial holes 54 of the gripping tube, seals 148 in an elastomeric material being housed around the outlets 155 to ensure a good sealing between the gripping tube and the inner structure 156.

A thin circular groove 54 intersecting the distribution holes 54 may be present to make the irrigation of the buffer area more homogeneous for effective disinfection over the entire gripping surface 3.

In one embodiment, the tank is housed inside the handle as in the partially tubular wall 52 comprising an output connector 58 connected to the duct 57.

In another embodiment, the tank 11 is housed in a handle casing 19 fixed to the leaf, as illustrated in FIGS. 14 and 15. The casing may comprise a window 157 in its front face, arranged to allow seeing the filling level of the tank 11. A gauge with possibly the presence of a colored floating element can be used to facilitate the visualization of the level of the liquid.

In other embodiments, the tank may also be in the form of a tank independent of the handle or of the handle casing 19, and connected to the handle 2 by a line. The tank 11 can be an exchangeable removable cartridge or a fixed reloadable tank, for example housed in the handle 2 or in the handle casing 19. A pump 59 is disposed between the tank and the manifold to supply the application member with liquid before each cleaning cycle. The pump may be a peristaltic-type pump which compresses the flexible and elastic duct 57. However, other types of pump can be provided such as a piston pump, a diaphragm pump or the like.

In the preferred embodiment, the device is energy-autonomous for the liquid supply by the pump 59 and for the displacement of the application member during the cleaning cycle. In addition, the device is primarily mechanical so that it can be disposed against the leaf without necessarily resorting to a power supply.

For that, the device comprises a member for accumulating mechanical energy and for restoring and transmitting mechanical energy 60 (called "energy and driving member" hereinafter) to the application member whose principle given by way of preferred example is as follows. The energy and driving member 60 is thus configured to store the mechanical energy actuating the handle during its pivoting about the axis J during its lowering for the opening of the opening of the leaf. Thus, the handle comprises a tubular bracket 61 for receiving the energy and driving member 60 and for the kinematic connection between the door closing mechanism and the application member. The bracket 61 of the member is substantially perpendicular to the tubular wall 52 and to the wall of the gripping surface and comprises a frame 62 housed inside the tubular bracket on which a speed multiplication mechanism 63 connected to the side rail 111 of the door closing mechanism is mounted upstream. The speed multiplication mechanism 63 is configured to drive an output shaft 65 of the mechanism over a little more than 360 degrees when the side rail 111 of the door closing mechanism is pivotally urged at an angle of less than 180 degrees (for example about 20° to 40°) corresponding to the stroke of the lowering of the handle during the opening of the door. The upstream multiplication mechanism 63 consists of a wheel gearing and pinions whose design is within the reach of those skilled in the art. Particularly, the mechanism 63 comprises a ring gear 140 formed in the wall of the leaf 9 in which a planet gear 141 is meshed. The planet gear 141 is mounted on a shaft 142 which carries a gear formed by a first pinion 143 which drives a second pinion 144 mounted on the output shaft 65 of the mechanism. The mechanism 63 thus transmits a torque to a first one-way or backstopping clutch 66 formed of an upstream notched portion 67 and a downstream notched portion 68 capable of transmitting a torque in the downstream direction only. The two notched portions 67, 68 cooperate between a coupled position in which the torque is transmitted from the upstream notched portion 67 to the notched portion 68 and an uncoupled position where no torque is transmissible back from the downstream notched portion 68 to the upstream notched portion 67. The backstopping effect of the clutch is obtained by an asymmetrical engagement of the teeth of the notched portions 67, 68, configured in such a way as to create a mechanical coupling in only one rotational direction and an uncoupling in the opposite direction. The downstream portion 68 of the clutch is secured to the peristaltic pump 59 which comprises a rotary disc portion 69 driven by the torque transmitted by the clutch with an annular groove 72 in the disc portion as well as a fixed rigid tubular passage 71 in the frame for the passage of the flexible duct. The passage area comprises a cam 70 which periodically compresses the tube during each rotation of the rotary portion 69. The rotary portion 69 is itself secured to a set 73 of cyclic latches comprising an upstream latch 74 in the form of a wheel and a downstream latch 75 in the form of a wheel connected by a first main torsion spring 76. It should however be noted that the annular groove 72 is preferably omitted so as to facilitate the coupling and decoupling of the backstopping-effect clutch. The activation of the latches is set by a camshaft 77 disposed along the member. The camshaft 77 comprises a first tooth 78 disposed on the shaft and in the vicinity of the upstream portion 67 of the clutch for engaging a finger 79 disposed on the surface of this portion.

The camshaft 77 also comprises a second tooth 80 on which a torsion spring 76 can bear to be prevented from expanding when the handle returns to the rest position (preferably horizontally). Finally, the shaft 77 comprises a third tooth 81 which engages cyclically on a finger 82 of the downstream latch 75 so as to release the latch when the first tooth 78 is engaged with the finger 79 and therefore to restore the energy of the spring downstream on a transmission 83 connected to the worm screw which moves the application member.

The transmission 83 is driven by a shaft 84 connected to the assembly 73 of latches via a second two-way cyclic clutch 85 consisting of two notched portions 87, 88. This second clutch is configured to transmit a torque to the transmission 83 in the coupled position for the displacement of the application member on the gripping surface, forwardly in the end-of-stroke position and in the uncoupled position when returning to the supply position during the cleaning. The passage to the uncoupled position of the second clutch 85 is performed by means of a cam path 86 carried by the surface of the downstream portion 88 and of a finger 89 supported by the frame of the handle. The coupled (FIGS. 27*a*, 27*b*) and uncoupled (FIGS. 27*c*, 27*d*) positions can have stable positions created by an elastic element on one portion, such as an elastic tab 159, engaging a protrusion or recess 160*a*, 160*b* on the other portion, in the two stable positions.

The energy and driving member comprises a second torsion spring 90 connected to the transmission shaft 84 and to the frame in order to provide the energy necessary for the return of the application member from its end-of-stroke position to its supply portion. The energy of this second spring is stored during the forward phase of the member for applying and restoring the energy of the first spring 76. This second spring 90 is tensioned as the first spring 76 expands. The second spring 90 is chosen with a lower stiffness constant than the first spring 76 so as to allow the storage of part of the energy by the second spring. The second spring could be replaced by any other type of spring such as a linear spring, having a constant or proportional return force, fixed for example directly to the support bushing 49. The two springs 76 and 90 could themselves be constant or quasi-constant torque springs.

The transmission or multiplier 83 at the output of the energy and driving member can be achieved by a gear of at least two pinions 91, 92 arranged at 90 degrees or any suitable angle and optionally a secondary gear with a wheel 93 coaxial with the output pinion 92 and meshing a pinion 94 coupled to the worm screw. Any other suitable transmission allowing the driving and accurate adjustment of the stroke of the bushing between the two stroke positions 46, 48 of the bushing is possible.

According to one advantageous aspect of the invention, the transmission is a transmission by a magnetic coupling. The driving nut 135 drives a magnet 139 which drives the bushing of the cleaning member 10, the bushing comprising a magnetized or ferromagnetic body for example housed inside the bushing. A rail 158 disposed in the inner structure 156 engages a complementary guide in the nut 135 in order to block the rotation of the nut and ensure its translational displacement only.

The rigid annular support (bushing) 49 may for example comprise or consist of a ferromagnetic material, or of a magnet having a polarization complementary to the magnetic polarization of the permanent magnet 139. In the example illustrated in FIG. 18, the rigid annular support 49 comprises a permanent magnet 139*b* housed between two ferromagnetic portions 49*a*, 49*b* of the annular support 49. The polarization of the magnet 139*b* on the bushing 49 is opposite to the polarization of the magnet 139 on the nut in the direction of translation (direction of the axis/of the nut).

The tubular collar 4 of the handle is made of a non-magnetic material.

In one embodiment comprising a permanent magnet on the application member 10, it can also be envisaged to have a ferromagnetic nut or one having a ferromagnetic portion instead of a magnet.

In order to avoid buttressing phenomena, the bushing can be coupled to a multitude of magnets distributed homogeneously in the bushing as well as in the internal perimeter of the gripping surface translated by one or more linear actuators (screw-nut or belt).

In one embodiment as illustrated, the rigid annular support 49 comprises flanges 49*a*, 49*b* at the axial ends of the support, the magnetic coupling of the flanges to the nut also allowing avoiding buttressing of the bushing.

This magnetic coupling provides security for the mechanism since a translation of the ring by the user has no impact on the mechanism located in the door handle. In addition, if in a particular case the user keeps his hand on the handle during the disinfection phase, the ring blocked by the user's hand is decoupled from the nut and does not hinder the user: the ring does not exert a force on the hand which remained on the handle.

The general operation of the energy and driving member is as follows. During the lowering of the handle 2, the first one-way clutch 66 is in the coupling position. The upstream latch 74 is in the free position while the downstream latch 75 is in the blocked position. The set of cyclic latches 73 thus isolates the main torsion spring 76 which is tensioned and stores the mechanical energy of the handle lowering movement. The second two-way clutch 85 is preferably in the coupled position. During this phase, the application member 10 is in the supply position opposite the liquid distribution manifold. During this phase of rotation over approximately one revolution, the peristaltic pump 59 is also actuated in rotation thereby engaging the cam 70 on the duct so that the liquid is pumped from the tank to the applicator pad thus filling it with cleaning liquid.

When the handle is disengaged and rises from its lowered position, the first backstopping clutch 66 is uncoupled and the set of latches is blocked by the mechanism 81, 82 of the camshaft. Arrived at the final displacement position of the handle, the finger 79 pushes the teeth 78 and 81, thus freeing the finger 82 and the first torsion spring 76. The first torsion spring 76 is then released and the finger 82 of the downstream wheel 75 of the latch is released which allows the transmission of the torque stored by the expansion of the spring to the downstream transmission or multiplier 83. The application member is consequently moved from the supply position to the end-of-stroke position, thus allowing the cleaning of the handle. During this phase, the clutch is in the coupled position and the first spring 76 tensions the second spring 90 which therefore stores energy in this forward phase of the member 10.

Once the application member 10 has reached the end-of-stroke position, the second spring is tensioned to its maximum tension. The downstream wheel 75 of the cyclic latch 73 is then not yet in the blocked position. The second cyclic clutch 66 is uncoupled at the end of this first rotation, the downstream wheel 75 is not yet blocked. The second cyclic clutch 85 is then uncoupled (the finger 89 engaged in the cam path 86 moves the toothed portions 87, 88 of the clutch apart from each other). The second spring 90 expands thereby driving the transmission in the opposite direction and driving the application member 10 which returns to the supply position.

Once the member is in the supply position, the handle is at rest and a new supply and cleaning cycle can start again when the handle is lowered again by a user.

It should be noted that the device can operate with two opposite handles and disposed on either side of the leaf. The device is perfectly energy-autonomous and this energy is renewable since it only originates from muscle strength.

It should be noted that the energy and actuation member of the embodiment of FIGS. 10 to 27 could however replace an actuation unit comprising an electronic controller, an electric actuation motor or by using a linear motor, optionally one or more position sensors of the annular ring, and also optionally a handle energy recovery member, an electrical energy transformation and storage member for the supply of the electrical and electronic elements of the device.

Figure 28:
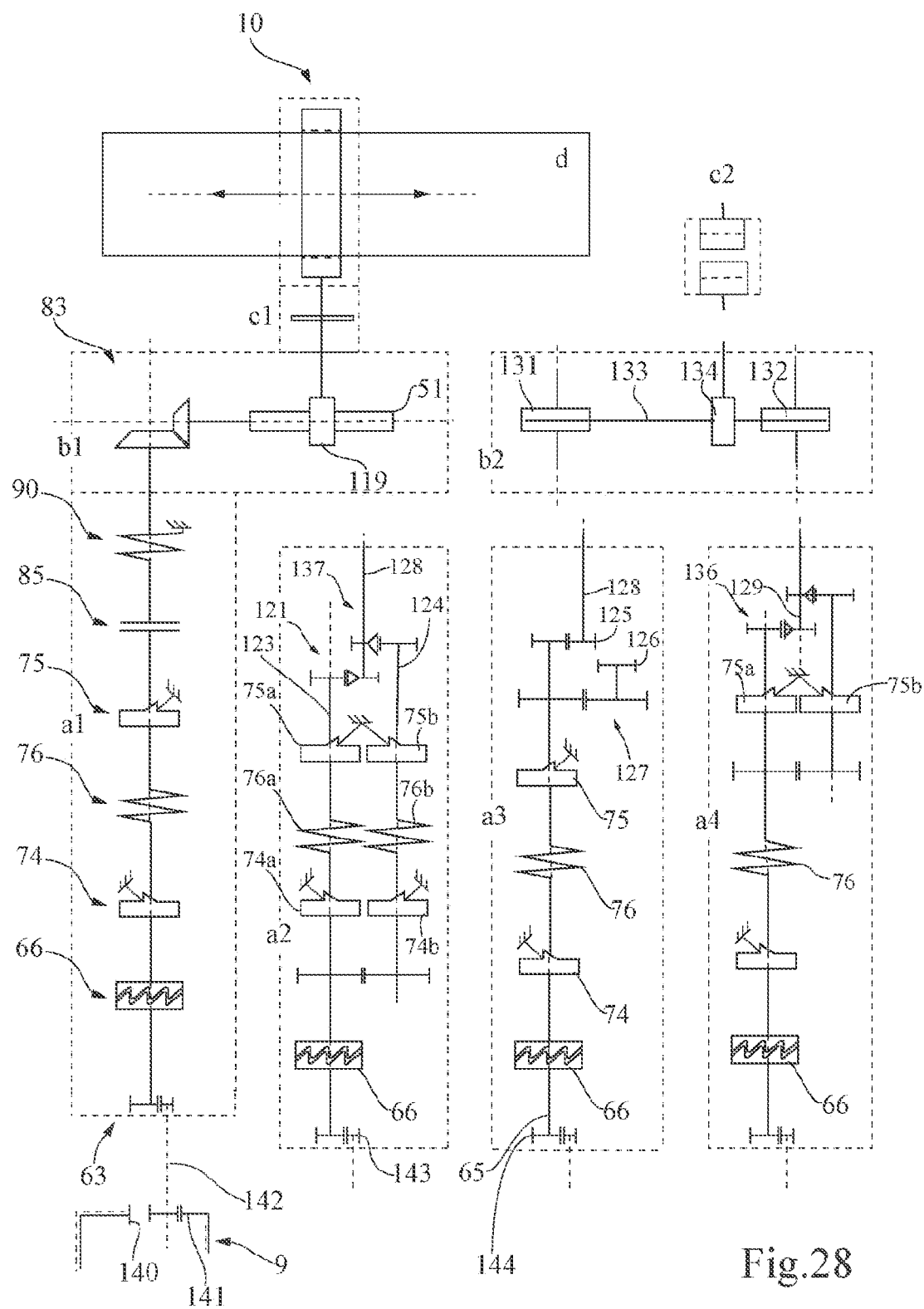
FIG. 28 is a schematic and kinematic illustration of different possible embodiments of the device according to different selected modules of the mechanical energy accumulation and restoration member and the transmission and coupling means.

FIG. 28 represents several possible combinations of modules of the device with mechanical energy storage and restoration.

In general, the device comprises a mechanical energy accumulation and restoration member in the form of a storage and reversing block a1, a2, a3 or a4. The storage and reversing block is connected to a translation block b1 or b2 and to a coupling block c1 or c2 which can be connected to the application member 10 or the gripping surface 3. The storage and reversing a1-a4, translation b1-b2 and coupling c1-c2 blocks can be selected according to different possible combinations.

According to a first configuration of the device, the storage and reversing block a1, the translation block b1 and the coupling block c1 form part of the device described in the embodiment of FIGS. 18 to 27. The same references are used to designate the same elements.

Other embodiments can be envisaged, the storage and reversing blocks a1, a2, a3 and a4 being interchangeable, as well as the translation blocks b1 and b2 and the coupling blocks c1 and c2.

For example, a combination a2-b1-c2 is a possible solution. The speed reducers and multipliers as well as the latch teeth opening mechanisms are not represented in this figure. Each element is represented schematically, without anchoring to a reference and without concern for the scale.

The storage and reversing block a2 consists (in order of actuation) of a backstopping clutch coupled at the output to the first spring 76a which is itself blocked by a system of latches/teeth 75a at the input and at the output thereof, just like for the block a1. This system allows the spring to be wound during the lowering of the handle without being unwound during the raising of the latter. At the same time, a second blocked spring system 76b, between two latches/teeth 74b, 75b is also wound when the user actuates the handle pivotally (for example for the lowering during the opening/closing of the leaf). Two one-way gears 136, 137 (coupled in one direction of rotation, freewheeling in the other direction of rotation) are disposed at the output of the shafts so that the first shaft 123 drives the ring in its forward phase while the second shaft 124 drives the ring in its return phase, without coupling of the shaft 124 during the forward phase and without coupling of the shaft 123 in the return phase.

When the tooth of the output latch 75a of the first spring 76a is open, the latter discharges thereby driving the ring of the application member 10 in its forward phase. Once at the end of the stroke, the tooth of the output latch 75b of the second spring 76b is in turn open, driving the ring in its return phase. The teeth of the latches are cyclically opened by a camshaft system moved by the central shaft (not illustrated). They are generally passively closed by return springs immediately after having being opened.

The storage and reversing block a3 is very similar to the block a1, except that the reversal of the direction of rotation is done with a reversing means similar to a gearbox system. The ring of the application member switches from the forward phase to the return phase when the pinion 125 linked to the output shaft 128 is moved relatively in translation to be coupled with the pinion 126 of the second shaft 127 which for its part rotates in the opposite direction. In which case, the spring must ensure the back and forth motion of the ring during its expansion.

The storage and reversing block a4 is a combination of the blocks a2 and a3. The single spring 76 is used here to move the ring of the application member in its forward and return phase, just like for the block a3. However, the means for reversing the direction of rotation made by translation of the output pinion 129 may be more complex than a double check system, this last solution is applied here just like in the block a2.

The translation block b2 represents a translation of the cleaning ring made by a pulley 131, 132 and belt 133 system.

The coupling block c2 represents a magnetic coupling. The nut 135 of the worm screw or of the connection element 134 is secured to a magnet; both translating in a closed system. The ring in which a system of magnets or ferrous bodies is inserted is then magnetically coupled to the magnet of the nut 135 or of the element 134. Several magnet c2 and translation (b1 or b2) blocks may be necessary for the ring to be properly guided.

Many other versions can be imagined, for example storing the energy during the lowering and the raising of the handle, also composed of check systems, reversers, and toothed latches similar to those presented in the blocks a1, a2, a3 and a4.

| List of the references in the figures |
|---|
| leaf 9 |
|   opening mechanism (not visible) |
|   wall of the leaf (not represented) |
| cleaning device 1 |
|   handle casing 19 |
|     window 157 |
|   return spring 147 |
|   handle 2 |
|     inner structure 156 |
|       liquid outlets 155 |
|       rail 158 |
|     gripping tube/gripping surface 3 |
|     collar 4 |
|       end portions 5, 6 |
|       central core 7 |
|     pivot axis 8 |
|     inclined plane 117 |
|   supply area 46 |
|     supply position 47 |
|       liquid distribution manifold 27 |
|         liquid outlets 54 |
|           orifices 54 |
|           groove 54a |
|         seal 148 |
|     end-of-stroke position 48 |
|     partially tubular wall 52 |
|       longitudinal through-passage 53 |
|     tubular bracket 61 |
|       frame 62 |
|   application/cleaning member 10 |
|   (in the form of a bushing) |
|     buffer reserve 24 |
|       applicator pad 25 |
|       split ring 26 |
|         slot 26a |
|         support ring |
|         material/pad strip |
|     rigid annular support 49 |
|       base 49a |
|         flange 49c |
|         radial coating 49d |
|         hole 149 |
|       cover 49b |
|       unlockable fixing mechanism 152, 154 |
|       base 50 |
|         nut 135 |
| liquid tank 11 |
|   cleaning solution |
| (liquid)supply means 12 |
|   liquid pump 13 |
|     piston 114 |
|     chamber 115 |
|     spring 120 |
|     finger 116 |
|     intake check valve 118 |
|     discharge check valve 119 |
|       ball 121 |
|       coil spring 122 |
|   line 14 |
|   connector 56 |
|   duct 57 |
|   output connector 58 |
|   pump 59 (peristaltic pump) |
|     rotary disk portion 69 |
|       annular groove 72 |
|       cam 70 |
|     fixed rigid tubular passage 71 |
| sensor 15 (of presence) |
| actuation unit 16 |
|   electronic controller 17 |
|   driving means 18 |
|     electric motor 20 |
|       worm screw 51 |
|       nut 135 |
|         permanent magnet 139 |
|   energy recovery member 96 |
|     generator for converting mechanical energy into electrical energy 44 |
|       transmission shaft 98 |
|         pinion 138 |
|         cylinder 107 |
|           through-slots 108, 109 |
|           central through-bore 110 |
|       gear 145 (ex. toothed disk portion) |
|       collar 99 |
|         flange 101 |
|           holes 102 |
|         connecting part 103 |
|         proximal end 104 |
|         transmission bars, for example two parallel bars 105, 106 |
|     torque transmission mechanism 64 |
|     electrical energy accumulator 45 |
|     tubular bracket 97 |
|       housing 113 |
|       key 112 |
|       side rail 111 |
|   energy and driving member 60 |
|     speed multiplication mechanism 63 |
|       output shaft 65 |
|       ring gear 140 |
|       planet gear 141 |
|       shaft 142 |
|       first pinion 143 |
|       second pinion 144 |
|     first one-way or backstopping clutch 66 |
|       upstream notched portion 67 |
|       downstream notched portion 68 |
|     set 73 of cyclic latches |
|       upstream latch 74 |
|       downstream latch 75 |
|         finger 82 |
|     first main torsion spring 76 |
|     camshaft 77 |
|       first tooth 78 |
|       second tooth 80 |
|       third tooth 81 |
|       finger 79 |
|     transmission 83 |
|     shaft 84 |
|     second two-way cyclic clutch 85 |
|       downstream portion 88 |
|       cam finger 89 |
|       cam path 86 |
|       elastic tab 159 |
|       second torsion spring 90 |
|     pinions 91, 92 arranged at 90 degrees |
|     wheel 93 |
|     pinion 94 |
| mechanical energy accumulation and restoration member |
|   storage and reversing block a1, a2, a3 or a4 |
|   translation block b1 or b2 |
|   coupling block c1 or c2 |
|   one-way gears 136, 137 |
|   first shaft 123 |
|   second shaft 124 |
|   pinion 125 |
|   output shaft 128 |
|   pinion 126 |
|   second shaft 127 |
|   output pinion 129 |
|   pulley 131, 132 and belt 133 system |
|     connection element de 134 |
| unlocking tool 150 |
|   pin 151 |
| first step 100 |
| second step of detecting the stopping of the action on the handle 200 |
| the next step 300 |
| the next step 400 |

-continued

List of the references in the figures longitudinal axis J of the bracket (pivot axis of the handle)
axis I
angle A

The invention claimed is:

1. A handle cleaning device comprising
at least one handle comprising a gripping surface to be cleaned forming part of a tubular or partially tubular-shaped wall,
an application member for applying a cleaning liquid on the gripping surface, and
cleaning liquid supply means for supplying cleaning liquid to the application member, the application member being formed at least in part of an annular bushing mounted around the gripping surface and comprising at least one buffer reserve arranged in contact with the gripping surface, and
a unit for actuating the application member comprising driving means configured to move the application member axially along said gripping surface between a distribution position for the transfer of cleaning liquid in the buffer reserve and an application configuration for the application of cleaning liquid on the gripping surface so as to apply cleaning liquid from the buffer reserve on the gripping surface during this displacement,
wherein the buffer reserve comprises an applicator pad in contact with the gripping surface having a porous structure or a liquid retention interstice structure for storing some said cleaning liquid and wherein the cleaning liquid supply means comprises a cleaning liquid distribution manifold comprising at least one liquid outlet facing the applicator pad in the distribution position.

2. The device according to claim 1, wherein the driving means configured to move the application member comprise a magnetic coupling.

3. The device according to claim 1, wherein the cleaning liquid distribution manifold comprises a plurality of liquid outlets distributed facing the applicator pad.

4. The device according to claim 1, wherein the driving means comprises
a belt and pulley assembly driving a magnet which drives the bushing of the application member, said bushing comprising a magnetized or ferromagnetic body, or a worm screw extending longitudinally inside the tubular wall of the gripping surface of the handle and a nut movable along the worm screw, the nut driving the magnet.

5. The device according to claim 1, wherein the cleaning liquid supply means comprises, or is configured to couples with, at least one container for holding a supply of the cleaning liquid, wherein the cleaning liquid distribution manifold comprises at least one liquid inlet for receiving the cleaning liquid from the container, wherein the at least one liquid inlet is fluidly coupled to the at least one liquid outlet for distributing the cleaning liquid from the container to the application member via the at least one liquid outlet.

6. The device according to claim 5, wherein the actuating unit comprises an electronic controller configured to automatically control the action of the driving means for the relative displacement of the buffer reserve with the gripping surface and/or to control the liquid distribution by the supply means for filling with liquid the buffer reserve of the application member from the at least one container.

7. The device according to claim 6, wherein the liquid supply means comprises a liquid level sensor configured for measuring a level of liquid in said at least one container, the liquid level, sensor connected to the electronic controller.

8. The device according to claim 6, wherein the device comprises at least one sensor arranged to detect the presence of a touch of the handle by a user, said sensor being associated with the electronic controller which is configured to automatically actuate the liquid supply and/or driving means, in response to a detection information.

9. The device according to claim 8, wherein said at least one sensor comprises an optical sensor.

10. The device according to claim 5, wherein the at least one container of the liquid supply means is located above the handle, the delivery of a volume of liquid dispensed to the buffer reserve being made by the opening of a mechanically or electrically actuated valve to let the liquid pass only by the pressure due to the gravitational force.

11. The device according to claim 5, comprising a window arranged to allow seeing a fill level of the at least one container.

12. The device according to claim 11, wherein said at least one container comprises a gauge with a colored floating element to facilitate the visualization of the fill level through the window.

13. The device according to claim 5, wherein said at least one container is a removable container connected by detachable connection means to at least one connection interface of the supply means.

14. The device according to claim 1, wherein said device comprises at least one storage and reversing block or a member for recovering mechanical energy by torque transmission means due to the rotation of the handle on a mechanism for opening and/or closing a leaf, for the storage of this mechanical energy and/or electrical energy transformation and storage member and finally a member for redistributing this stored mechanical and/or electrical energy to the actuating unit or to the driving means or to an assembly formed of a translation block and a coupling block which control the displacement of the gripping surface or of the application member.

15. The device according to claim 1, wherein the liquid supply means comprise at least one pump actuated in an electronically monitored manner by an electronic unit or a mechanically monitored manner by mechanical actuation means during the actuation of the handle, preferably the pivoting thereof about its actuation axis for the actuation of a leaf opening/closing mechanism; said pump being preferably a peristaltic pump or a piston pump.

16. The device according to claim 1, wherein the buffer reserve comprises an applicator pad in contact with the gripping surface detachably mounted in a rigid support of the bushing in order to be able to replace or clean the applicator pad.

17. The device according to claim 16, wherein the applicator pad is in the form of a flexible split ring so as to be able to pass the handle through an open slot of the split ring.

18. The device according to claim 16, wherein the rigid support of the bushing comprises at least two separable portions, the two portions being locked together by an elastic or magnet fixing mechanism unlockable with a tool comprising a pin.

19. The device according to claim 16, wherein the rigid support comprises at least two separable portions, the two portions being locked together by a magnetic fixing mechanism.

20. The device according to claim 19, wherein the two portions of the rigid support of the bushing, comprise a base and a cover, the cover being housed in the base under an annular coating.

21. The device according to claim 19, further comprising an unlocking tool comprising a magnet producing a magnetic field stronger than the magnetic field of the fixing mechanism.

22. The device according to claim 1, wherein the annular bushing of the application member comprises at least one permanent magnet housed in a rigid support of the bushing, the rigid support comprising or consisting of a ferromagnetic material.

23. The device according to claim 1, wherein the gripping surface comprises a circular groove intersecting the at least one or plurality of liquid outlets.

\* \* \* \* \*